US008444693B2

(12) United States Patent
Reiley

(10) Patent No.: US 8,444,693 B2
(45) Date of Patent: May 21, 2013

(54) APPARATUS, SYSTEMS, AND METHODS FOR ACHIEVING LUMBAR FACET FUSION

(75) Inventor: Mark A. Reiley, San Jose, CA (US)

(73) Assignee: SI-Bone Inc., San Jose, CA (US)

( * ) Notice: Subject to any disclaimer, the term of this patent is extended or adjusted under 35 U.S.C. 154(b) by 145 days.

(21) Appl. No.: 12/960,811

(22) Filed: Dec. 6, 2010

(65) Prior Publication Data

US 2011/0125268 A1 May 26, 2011

Related U.S. Application Data

(63) Continuation-in-part of application No. 11/136,141, filed on May 24, 2005, now Pat. No. 7,922,765, and a continuation-in-part of application No. 10/914,629, filed on Aug. 9, 2004, now abandoned.

(51) Int. Cl.
*A61F 2/44* (2006.01)

(52) U.S. Cl.
USPC ........................................ 623/17.11; 606/246

(58) Field of Classification Search
USPC ................. 606/246, 279, 95, 96, 98, 99, 104; 623/17.11–17.16
See application file for complete search history.

(56) References Cited

U.S. PATENT DOCUMENTS

| | | | |
|---|---|---|---|
| 2,414,882 A | 7/1947 | Longfellow | |
| 3,076,453 A | 2/1963 | Tronzo | |
| 4,344,190 A | 8/1982 | Lee et al. | |
| 4,501,269 A | 2/1985 | Bagby | |
| 4,569,338 A | 2/1986 | Edwards | |
| 4,612,918 A | 9/1986 | Slocum | |
| 4,657,550 A | 4/1987 | Daher | |
| 4,773,402 A | 9/1988 | Asher et al. | |
| 4,834,757 A | 5/1989 | Brantigan | |
| 4,878,915 A | 11/1989 | Brantigan | |
| 4,950,270 A | 8/1990 | Bowman et al. | |
| 4,961,740 A | 10/1990 | Ray et al. | |
| 5,034,011 A | 7/1991 | Howland | |
| 5,035,697 A | 7/1991 | Frigg | |
| 5,102,414 A * | 4/1992 | Kirsch | 606/53 |
| 5,108,397 A | 4/1992 | White | |
| 5,122,141 A | 6/1992 | Simpson et al. | |

(Continued)

FOREIGN PATENT DOCUMENTS

EP 1287796 A1 3/2003

(Continued)

OTHER PUBLICATIONS

Al-Khayer et al.; Percutaneous sacroiliac joint arthrodesis, a novel technique; J Spinal Disord Tech; vol. 21; No. 5; pp. 359-363; Jul. 2008.

(Continued)

*Primary Examiner* — Eduardo C Robert
*Assistant Examiner* — Christina Negrellirodriguez
(74) *Attorney, Agent, or Firm* — Shay Glenn LLP

(57) ABSTRACT

Assemblies of one or more implant structures make possible the achievement of diverse interventions involving the fusion and/or stabilization of lumbar and sacral vertebra in a non-invasive manner, with minimal incision, and without the necessitating the removing the intervertebral disc. The representative lumbar spine interventions, which can be performed on adults or children, include, but are not limited to, lumbar interbody fusion; translaminar lumbar fusion; lumbar facet fusion; trans-iliac lumbar fusion; and the stabilization of a spondylolisthesis.

28 Claims, 19 Drawing Sheets

U.S. PATENT DOCUMENTS

| | | |
|---|---|---|
| 5,139,498 A | 8/1992 | Astudillo Ley |
| 5,147,367 A | 9/1992 | Ellis |
| 5,147,402 A | 9/1992 | Bohler et al. |
| 5,242,444 A | 9/1993 | MacMillan |
| 5,298,254 A | 3/1994 | Prewett et al. |
| 5,334,205 A | 8/1994 | Cain |
| 5,470,334 A | 11/1995 | Ross et al. |
| 5,480,402 A | 1/1996 | Kim |
| 5,569,249 A | 10/1996 | James et al. |
| 5,593,409 A | 1/1997 | Michelson |
| 5,609,636 A | 3/1997 | Kohrs et al. |
| 5,626,616 A | 5/1997 | Speece |
| 5,645,599 A | 7/1997 | Samani |
| 5,667,510 A | 9/1997 | Combs |
| 5,669,909 A | 9/1997 | Zdeblick et al. |
| 5,672,178 A | 9/1997 | Petersen |
| 5,713,904 A | 2/1998 | Errico et al. |
| 5,868,749 A | 2/1999 | Reed |
| 5,928,239 A | 7/1999 | Mirza |
| 6,010,507 A | 1/2000 | Rudloff |
| 6,053,916 A | 4/2000 | Moore |
| 6,096,080 A | 8/2000 | Nicholson et al. |
| 6,210,442 B1 | 4/2001 | Wing et al. |
| 6,214,049 B1 | 4/2001 | Gayer et al. |
| 6,221,074 B1 | 4/2001 | Cole et al. |
| 6,224,607 B1 | 5/2001 | Michelson |
| 6,241,732 B1 | 6/2001 | Overaker et al. |
| 6,270,528 B1 | 8/2001 | McKay |
| 6,302,885 B1 | 10/2001 | Essiger |
| 6,306,140 B1 | 10/2001 | Siddiqui |
| 6,451,020 B1 | 9/2002 | Zucherman et al. |
| 6,471,707 B1 | 10/2002 | Miller et al. |
| 6,485,518 B1 * | 11/2002 | Cornwall et al. ......... 623/17.11 |
| 6,497,707 B1 | 12/2002 | Bowman et al. |
| 6,517,541 B1 | 2/2003 | Sesic |
| 6,565,566 B1 | 5/2003 | Wagner et al. |
| 6,575,991 B1 | 6/2003 | Chesbrough et al. |
| 6,579,293 B1 | 6/2003 | Chandran |
| 6,582,431 B1 | 6/2003 | Ray |
| 6,595,998 B2 | 7/2003 | Johnson et al. |
| 6,602,293 B1 | 8/2003 | Biermann et al. |
| 6,605,090 B1 | 8/2003 | Trieu et al. |
| 6,635,059 B2 | 10/2003 | Randall et al. |
| 6,666,868 B2 | 12/2003 | Fallin |
| 6,669,529 B1 | 12/2003 | Scaries |
| 6,692,501 B2 | 2/2004 | Michelson |
| 6,723,099 B1 | 4/2004 | Goshert |
| 6,743,257 B2 | 6/2004 | Castro |
| 7,118,579 B2 | 10/2006 | Michelson |
| 7,211,085 B2 | 5/2007 | Michelson |
| 7,223,269 B2 | 5/2007 | Chappuis |
| 7,335,205 B2 | 2/2008 | Aeschlimann et al. |
| 7,452,359 B1 | 11/2008 | Michelson |
| 7,452,369 B2 | 11/2008 | Barry |
| 7,481,831 B2 | 1/2009 | Bonutti |
| 7,569,054 B2 | 8/2009 | Michelson |
| 7,648,509 B2 | 1/2010 | Stark |
| 7,686,805 B2 | 3/2010 | Michelson |
| 7,708,761 B2 | 5/2010 | Petersen |
| 7,850,732 B2 | 12/2010 | Heinz |
| 7,857,832 B2 | 12/2010 | Culbert et al. |
| 7,887,565 B2 | 2/2011 | Michelson |
| 7,909,832 B2 | 3/2011 | Michelson |
| 7,922,765 B2 | 4/2011 | Reiley |
| 8,066,705 B2 | 11/2011 | Michelson |
| 8,066,709 B2 | 11/2011 | Michelson |
| 2001/0049529 A1 | 12/2001 | Cachia et al. |
| 2002/0038123 A1 | 3/2002 | Visotsky et al. |
| 2002/0049497 A1 | 4/2002 | Mason |
| 2002/0120275 A1 | 8/2002 | Schmieding et al. |
| 2002/0128652 A1 | 9/2002 | Ferree |
| 2002/0143335 A1 | 10/2002 | von Hoffmann et al. |
| 2002/0151903 A1 | 10/2002 | Takei et al. |
| 2002/0183858 A1 | 12/2002 | Contiliano et al. |
| 2002/0198527 A1 | 12/2002 | Mückter |
| 2003/0032961 A1 * | 2/2003 | Pelo et al. ......... 606/72 |
| 2003/0065332 A1 | 4/2003 | TenHuisen et al. |
| 2003/0233147 A1 | 12/2003 | Nicholson et al. |
| 2004/0024458 A1 | 2/2004 | Senegas et al. |
| 2004/0073216 A1 | 4/2004 | Lieberman |
| 2004/0073314 A1 | 4/2004 | White et al. |
| 2004/0087948 A1 | 5/2004 | Suddaby |
| 2004/0106925 A1 | 6/2004 | Culbert |
| 2004/0117022 A1 | 6/2004 | Marnay et al. |
| 2004/0127990 A1 | 7/2004 | Bartish, Jr. et al. |
| 2004/0147929 A1 | 7/2004 | Biedermann et al. |
| 2004/0181282 A1 | 9/2004 | Zucherman et al. |
| 2004/0225360 A1 | 11/2004 | Malone |
| 2005/0033435 A1 | 2/2005 | Belliard et al. |
| 2005/0107878 A1 | 5/2005 | Conchy |
| 2005/0124993 A1 | 6/2005 | Chappuis |
| 2005/0159749 A1 | 7/2005 | Levy et al. |
| 2005/0165398 A1 | 7/2005 | Reiley |
| 2005/0228384 A1 | 10/2005 | Zucherman et al. |
| 2005/0246021 A1 | 11/2005 | Ringeisen et al. |
| 2006/0036251 A1 | 2/2006 | Reiley |
| 2006/0054171 A1 | 3/2006 | Dall |
| 2006/0058793 A1 | 3/2006 | Michelson |
| 2006/0111779 A1 | 5/2006 | Petersen |
| 2006/0129247 A1 | 6/2006 | Brown et al. |
| 2006/0241776 A1 | 10/2006 | Brown et al. |
| 2006/0293662 A1 | 12/2006 | Boyer, II et al. |
| 2007/0083265 A1 | 4/2007 | Malone |
| 2007/0149976 A1 * | 6/2007 | Hale et al. ......... 606/85 |
| 2007/0156241 A1 | 7/2007 | Reiley et al. |
| 2007/0250166 A1 | 10/2007 | McKay |
| 2007/0270879 A1 | 11/2007 | Isaza et al. |
| 2008/0021454 A1 | 1/2008 | Chao et al. |
| 2008/0021455 A1 | 1/2008 | Chao et al. |
| 2008/0021456 A1 | 1/2008 | Gupta et al. |
| 2008/0021461 A1 | 1/2008 | Barker et al. |
| 2008/0065215 A1 | 3/2008 | Reiley |
| 2008/0154316 A1 | 6/2008 | Reiley |
| 2008/0154374 A1 | 6/2008 | Labrom |
| 2008/0161810 A1 | 7/2008 | Melkent |
| 2008/0234758 A1 | 9/2008 | Fisher et al. |
| 2008/0255618 A1 | 10/2008 | Fisher et al. |
| 2008/0255622 A1 | 10/2008 | Mickiewicz et al. |
| 2008/0255666 A1 | 10/2008 | Fisher et al. |
| 2008/0255667 A1 | 10/2008 | Horton |
| 2008/0275454 A1 | 11/2008 | Geibel |
| 2008/0306554 A1 | 12/2008 | McKinley |
| 2009/0018660 A1 | 1/2009 | Roush |
| 2009/0024174 A1 | 1/2009 | Stark |
| 2009/0036927 A1 | 2/2009 | Vestgaarden |
| 2009/0099602 A1 | 4/2009 | Aflatoon |
| 2009/0099610 A1 | 4/2009 | Johnson et al. |
| 2009/0131986 A1 | 5/2009 | Lee et al. |
| 2009/0138053 A1 | 5/2009 | Assell et al. |
| 2009/0157119 A1 | 6/2009 | Hale |
| 2009/0163920 A1 | 6/2009 | Hochschuler et al. |
| 2009/0216238 A1 | 8/2009 | Stark |
| 2009/0259261 A1 | 10/2009 | Reiley |
| 2009/0270929 A1 | 10/2009 | Suddaby |
| 2009/0287254 A1 | 11/2009 | Nayet et al. |
| 2009/0312798 A1 | 12/2009 | Varela |
| 2010/0094290 A1 | 4/2010 | Vaidya |
| 2010/0106194 A1 | 4/2010 | Bonutti et al. |
| 2010/0114174 A1 | 5/2010 | Jones et al. |
| 2010/0191292 A1 | 7/2010 | DeMeo et al. |
| 2010/0268228 A1 | 10/2010 | Petersen |
| 2010/0286778 A1 | 11/2010 | Eisermann et al. |
| 2010/0292738 A1 | 11/2010 | Reiley |
| 2011/0009869 A1 | 1/2011 | Marino et al. |
| 2011/0022089 A1 | 1/2011 | Assell et al. |
| 2011/0040362 A1 | 2/2011 | Godara et al. |
| 2011/0087294 A1 | 4/2011 | Reiley |
| 2011/0087296 A1 | 4/2011 | Reiley et al. |
| 2011/0118785 A1 | 5/2011 | Reiley |
| 2011/0118790 A1 | 5/2011 | Reiley |
| 2011/0118796 A1 | 5/2011 | Reiley et al. |
| 2011/0118841 A1 | 5/2011 | Reiley |
| 2011/0184518 A1 | 7/2011 | Trieu |
| 2011/0184519 A1 | 7/2011 | Trieu |
| 2011/0184520 A1 | 7/2011 | Trieu |

| | | | |
|---|---|---|---|
| 2011/0230966 A1 | 9/2011 | Trieu | |
| 2011/0238181 A1 | 9/2011 | Trieu | |
| 2011/0264229 A1 | 10/2011 | Donner | |

FOREIGN PATENT DOCUMENTS

| | | |
|---|---|---|
| JP | 05-176942 A | 7/1993 |
| JP | 2004512895 | 4/2004 |
| JP | 2004516866 | 6/2004 |
| WO | WO02/38054 | 5/2002 |
| WO | WO2004/002344 | 1/2004 |
| WO | WO2006003316 | 1/2006 |

OTHER PUBLICATIONS

Wise et al.; Minimally invasive sacroiliac arthrodesis, outcomes of a new technique; J Spinal Disord Tech; vol. 21; No. 8; pp. 579-584; Dec. 2008.

Reiley, Mark A.; U.S. Appl. No. 13/078,530 entitled "Systems and methods for the fixation or fusion of bone," filed Apr. 1, 2011.

Reiley, Mark A.; U.S. Appl. No. 12/357,483 entitled "Systems and methods for the fixation or fusion of bone in the hand and wrist," filed Jan. 22, 2009 (abandoned).

* cited by examiner

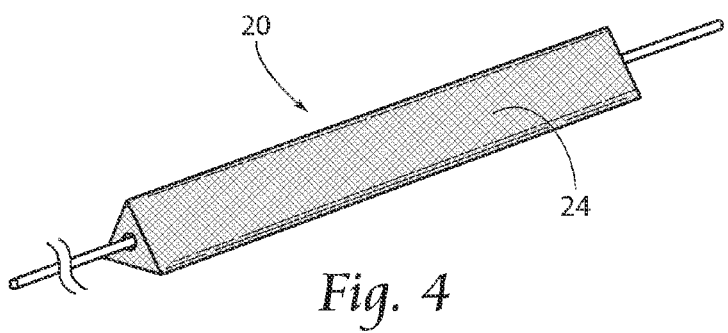
*Fig. 4*
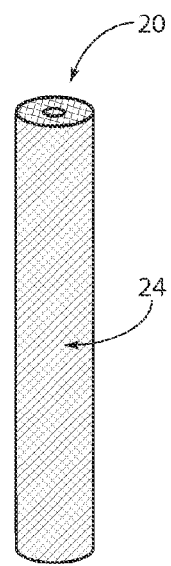 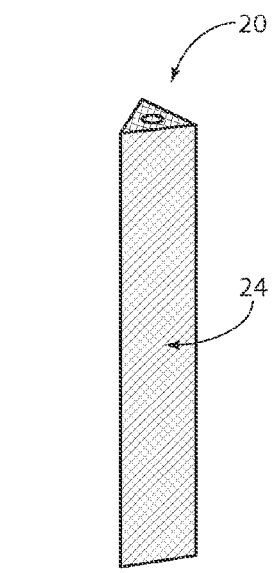 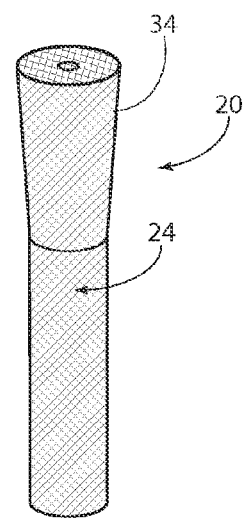
*Fig. 5*  *Fig. 6*  *Fig. 7*
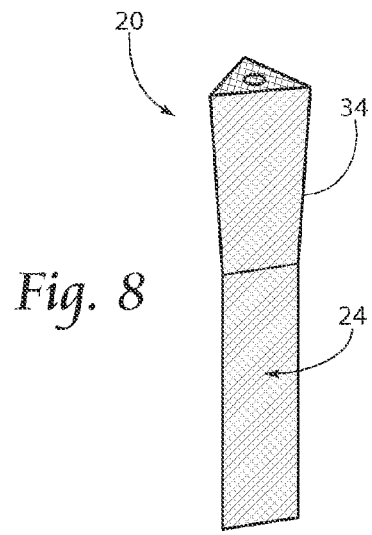
*Fig. 8*

Translaminar
Lumbar Fusion
(Posterior Approach)

Lumbar Facet Fusion (Posterior Approach)

APPARATUS, SYSTEMS, AND METHODS FOR ACHIEVING LUMBAR FACET FUSION

RELATED APPLICATIONS

This application is a continuation-in-part of co-pending U.S. patent application Ser. No. 11/136,141, filed May 24, 2005, which is a continuation-in-part of U.S. patent application Ser. No. 10/914,629, filed Aug. 9, 2004 (now abandoned).

FIELD OF THE INVENTION

This application relates generally to the stabilization of the lumbar spine.

BACKGROUND OF THE INVENTION

The spine (see FIG. 1) is a complex interconnecting network of nerves, joints, muscles, tendons and ligaments, and all are capable of producing pain.

The spine is made up of small bones, called vertebrae. The vertebrae protect and support the spinal cord. They also bear the majority of the weight put upon the spine.

Between each vertebra is a soft, gel-like "cushion," called an intervertebral disc. These flat, round cushions act like shock absorbers by helping absorb pressure and keep the bones from rubbing against each other. The intervertebral disc also binds adjacent vertebrae together. The intervertebral discs are a type of joint in the spine. Intervertebral disc joints can bend and rotate a bit but do not slide as do most body joints.

Each vertebra has two other sets of joints, called facet joints (see FIG. 2). The facet joints are located at the back of the spine (posterior). There is one facet joint on each lateral side (right and left). One pair of facet joints faces upward (called the superior articular facet) and the other pair of facet joints faces downward (called the inferior articular facet). The inferior and superior facet joints mate, allowing motion (articulation), and link vertebrae together. Facet joints are positioned at each level to provide the needed limits to motion, especially to rotation and to prevent forward slipping (spondylolisthesis) of that vertebra over the one below.

In this way, the spine accommodates the rhythmic motions required by humans to walk, run, swim, and perform other regular movements. The intervetebral discs and facet joints stabilize the segments of the spine while preserving the flexibility needed to turn, look around, and get around.

Degenerative changes in the spine can adversely affect the ability of each spinal segment to bear weight, accommodate movement, and provide support. When one segment deteriorates to the point of instability, it can lead to localized pain and difficulties. Segmental instability allows too much movement between two vertebrae. The excess movement of the vertebrae can cause pinching or irritation of nerve roots. It can also cause too much pressure on the facet joints, leading to inflammation. It can cause muscle spasms as the paraspinal muscles try to stop the spinal segment from moving too much. The instability eventually results in faster degeneration in this area of the spine. Degenerative changes in the spine can also lead to spondylolysis and spondylolisthesis. Spondylolisthesis is the term used to describe when one vertebra slips forward on the one below it. This usually occurs because there is a spondylolysis (defect) in the vertebra on top. For example, a fracture or a degenerative defect in the interarticular parts of lumbar vertebra L1 may cause a forward displacement of the lumbar vertebra L5 relative to the sacral vertebra S1 (called L5-S1 pondylolisthesis). When a spondylolisthesis occurs, the facet joint can no longer hold the vertebra back. The intervertebral disc may slowly stretch under the increased stress and allow other upper vertebra to slide forward.

An untreated persistent, episodic, severely disabling back pain problem can easily ruin the active life of a patient. In many instances, pain medication, splints, or other normally-indicated treatments can be used to relieve intractable pain in a joint. However, in for severe and persistent problems that cannot be managed by these treatment options, degenerative changes in the spine may require a bone fusion surgery to stop both the associated disc and facet joint problems.

A fusion is an operation where two bones, usually separated by a joint, are allowed to grow together into one bone. The medical term for this type of fusion procedure is arthrodesis.

Lumbar fusion procedures have been used in the treatment of pain and the effects of degenerative changes in the lower back. A lumbar fusion is a fusion in the S1-L5-L4 region in the spine.

One conventional way of achieving a lumbar fusion is a procedure called anterior lumbar interbody fusion (ALIF). In this procedure, the surgeon works on the spine from the front (anterior) and removes a spinal disc in the lower (lumbar) spine. The surgeon inserts a bone graft into the space between the two vertebrae where the disc was removed (the interbody space). The goal of the procedure is to stimulate the vertebrae to grow together into one solid bone (known as fusion). Fusion creates a rigid and immovable column of bone in the problem section of the spine. This type of procedure is used to try and reduce back pain and other symptoms.

Facet joint fixation procedures have also been used for the treatment of pain and the effects of degenerative changes in the lower back. These procedures take into account that the facet joint is the only true articulation in the lumbosacral spine. In one conventional procedure for achieving facet joint fixation, the surgeon works on the spine from the back (posterior). The surgeon passes screws from the spinous process through the lamina and across the mid-point of one or more facet joints.

Conventional treatment of spondylolisthesis may include a laminectomy to provide decompression and create more room for the exiting nerve roots. This can be combined with fusion using, e.g., an autologous fibular graft, which may be performed either with or without fixation screws to hold the bone together. In some cases the vertebrae are moved back to the normal position prior to performing the fusion, and in others the vertebrae are fused where they are after the slip, due to the increased risk of injury to the nerve with moving the vertebra back to the normal position.

Currently, these procedures entail invasive open surgical techniques (anterior and/or posterior). Further, ALIF entails the surgical removal of the disc. Like all invasive open surgical procedures, such operations on the spine risk infections and require hospitalization. Invasive open surgical techniques involving the spine continue to be a challenging and difficult area.

SUMMARY OF THE INVENTION

The invention provides apparatus, systems, and methods for the fusion and/or stabilization of the lumbar spine. The apparatus, systems, and methods include one or more elongated, stem-like implant structures sized and configured for the fusion or stabilization of adjacent bone structures in the lumbar region of the spine, either across the intervertebral disc or across one or more facet joints. Each implant structure includes a region formed along at least a portion of its length to promote bony in-growth onto or into surface of the structure and/or bony growth entirely through all or a portion of the structure. The bony in-growth or through-growth region along the surface of the implant structure accelerates bony in-growth or through-growth onto, into, or through the implant structure 20. The implant structure therefore provides extra-articular/intra osseous fixation, when bone grows in and around the bony in-growth or through-growth region. Bony in-growth or through-growth onto, into, or through the implant structure helps speed up the fusion and/or stabilization process of the adjacent bone regions fixated by the implant structure.

The assemblies of one or more implant structures make possible the achievement of diverse interventions involving the fusion and/or stabilization of lumbar and sacral vertebra in a non-invasive manner, with minimal incision, and without the necessitating the removing the intervertebral disc. The representative lumbar spine interventions, which can be performed on adults or children, include, but are not limited to, lumbar interbody fusion; translaminar lumbar fusion; lumbar facet fusion; trans-iliac lumbar fusion; and the stabilization of a spondylolisthesis.

BRIEF DESCRIPTION OF THE DRAWINGS

FIG. 4 is a perspective view of a representative embodiment of an elongated, stem-like, cannulated implant structure well suited for the fusion or stabilization of adjacent bone structures in the lumbar region of the spine, either across the intervertebral disc or across one or more facet joints.

FIGS. 5 to 8 are perspective views of other representative embodiments of implant structures well suited for the fusion or stabilization of adjacent bone structures in the lumbar region of the spine, either across the intervertebral disc or across one or more facet joints.

DESCRIPTION OF THE PREFERRED EMBODIMENT

Figure 1:
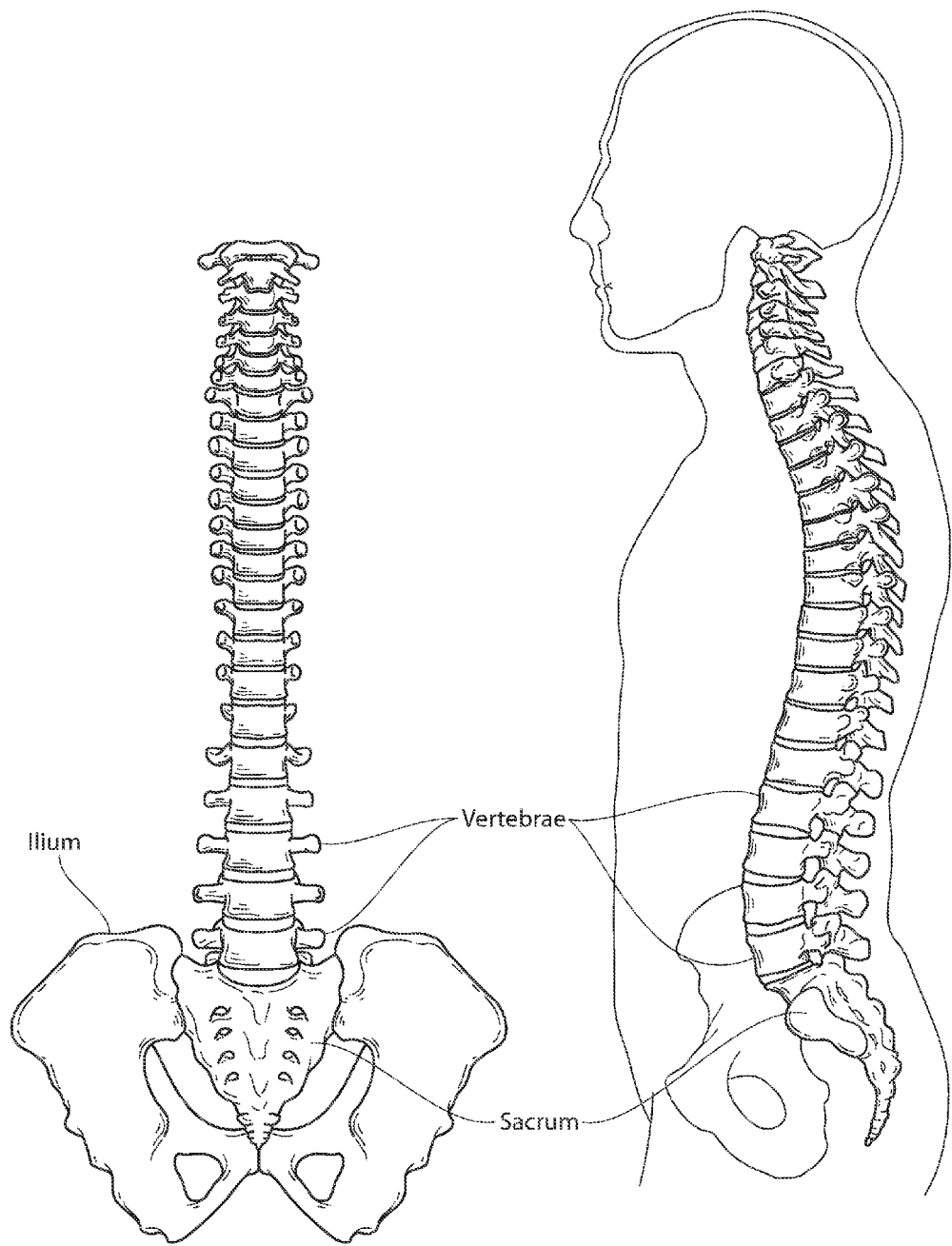
FIG. 1 are anatomic anterior and lateral views of a human spine.

Although the disclosure hereof is detailed and exact to enable those skilled in the art to practice the invention, the physical embodiments herein disclosed merely exemplify the invention that may be embodied in other specific structure. While the preferred embodiment has been described, the details may be changed without departing from the invention, which is defined by the claims.

I. The Implant Structure

FIG. 4 shows a representative embodiment of an elongated, stem-like, cannulated implant structure 20. As will be described in greater detail later, the implant structure 20 is sized and configured for the fixation of bones which are to be fused (arthrodesed) (i.e. fixation of two or more individual bones that are adjacent and/or jointed) and/or the stabilization of adjacent bone structures. In particular, and as will be demonstrated, the implant structure is well suited for the fusion or stabilization of adjacent bone structures in the lumbar region of the spine, either across the intervertebral disc or across one or more facet joints.

The implant structure 20 can be formed—e.g., by machining, molding, or extrusion—from a durable material usable in the prosthetic arts that is not subject to significant bio-absorption or resorption by surrounding bone or tissue over time. The implant structure 20, is intended to remain in place for a time sufficient to stabilize a bone fracture or fusion site. Such materials include, but are not limited to, titanium, titanium alloys, tantalum, tivanium (aluminum, vanadium, and titanium), chrome cobalt, surgical steel, or any other total joint replacement metal and/or ceramic, sintered glass, artificial bone, any uncemented metal or ceramic surface, or a combination thereof.

Alternatively, the implant structure 20 may be formed from a suitable durable biologic material or a combination of metal and biologic material, such as a biocompatible bone-filling material. The implant structure 20 may be molded from a flowable biologic material, e.g., acrylic bone cement, that is cured, e.g., by UV light, to a non-flowable or solid material.

The implant structure 20 is sized according to the local anatomy. The morphology of the local structures can be generally understood by medical professionals using textbooks of human skeletal anatomy along with their knowledge of the site and its disease or injury. The physician is also able to ascertain the dimensions of the implant structure 20 based upon prior analysis of the morphology of the targeted bone region using, for example, plain film x-ray, fluoroscopic x-ray, or MRI or CT scanning.

As FIGS. 5 to 8 show, the implant structure 20 can take various shapes and have various cross-sectional geometries. The implant structure 20 can have, e.g., a generally curvilinear (i.e., round or oval) cross-section——as FIG. 5 shows for purposes of illustration—or a generally rectilinear cross section (i.e., square or rectangular or hexagon or H-shaped or triangular—as FIG. 6 shows for purposes of illustration—or combinations thereof. In FIG. 4, the implant structure 20 is shown to be triangular in cross section, which effectively resists rotation and micromotion once implanted.

As FIGS. 7 and 8 show, the implant structure 20, whether curvilinear (FIG. 7) or rectilinear (FIG. 8) can include a tapered region 34 at least along a portion of its axial length, meaning that the width or diameter of the implant structure 20 incrementally increases along its axial length. Desirably, the tapered region 34 corresponds with, in use, the proximal region of the implant structure 20 (i.e., the last part of the implant structure 20 to enter bone). The amount of the incremental increase in width or diameter can vary. As an example, for an implant structure 20 having a normal diameter of 7 mm, the magnitude of the incremental increase at its maximum can range between about 0.25 mm to 1.25 mm. The tapered region 34 enhances the creation and maintenance of compression between bone segments or regions.

As FIG. 4 shows, the implant structure 20 includes a region 24 formed along at least a portion of its length to promote bony in-growth onto or into surface of the structure and/or bony growth entirely through all or a portion of the structure. The bony in-growth or through-growth region 24 along the surface of the implant structure 20 accelerates bony in-growth or through-growth onto, into, or through the implant structure 20. Bony in-growth or through-growth onto, into, or through the implant structure 20 helps speed up the fusion process of the adjacent bone regions fixated by the implant structure 20.

The bony in-growth or through-growth region 24 desirably extends along the entire outer surface of the implant structure 20, as shown in FIGS. 4 to 8. The bony in-growth region 24 or through-growth can comprise, e.g., through holes, and/or various surface patterns, and/or various surface textures, and/or pores, or combinations thereof. The configuration of the bony in-growth or through-growth region 24 can, of course, vary. By way of examples, the bony in-growth or through-growth region 24 can comprise an open mesh configuration; or beaded configuration; or a trabecular configuration; or include holes or fenestrations. Any configuration conducive to bony in-growth and/or bony through-growth will suffice.

The bony in-growth or through-growth region 24 can be coated or wrapped or surfaced treated to provide the bony in-growth or through-growth region, or it can be formed from a material that itself inherently possesses a structure conducive to bony in-growth or through-growth, such as a porous mesh, hydroxyapetite, or other porous surface. The bony in-growth or through-growth region can includes holes that allow bone to grow throughout the region.

In a preferred embodiment, the bony in-growth region or through-growth region 24 comprises a porous plasma spray coating on the implant structure 20. This creates a biomechanically rigorous fixation/fusion system, designed to support reliable fixation/fusion and acute weight bearing capacity.

The bony in-growth or through-growth region 24 may further be covered with various other coatings such as antimicrobial, antithrombotic, and osteoinductive agents, or a combination thereof. The entire implant structure 20 may be impregnated with such agents, if desired.

The implant structure includes an interior bore that accommodates its placement in a non-invasive manner by sliding over a guide pin, as will be described in greater detail later.

As before stated, the implant structure 20 is well suited for the fusion and/or stabilization of adjacent bone structures in the lumbar region of the spine. Representative examples of the placement of the implant structure 20 in the lumbar region of the spine will now be described.

A. Use of the Implant Structures to Achieve Anterior Lumbar Interbody Fusion

Figure 9:
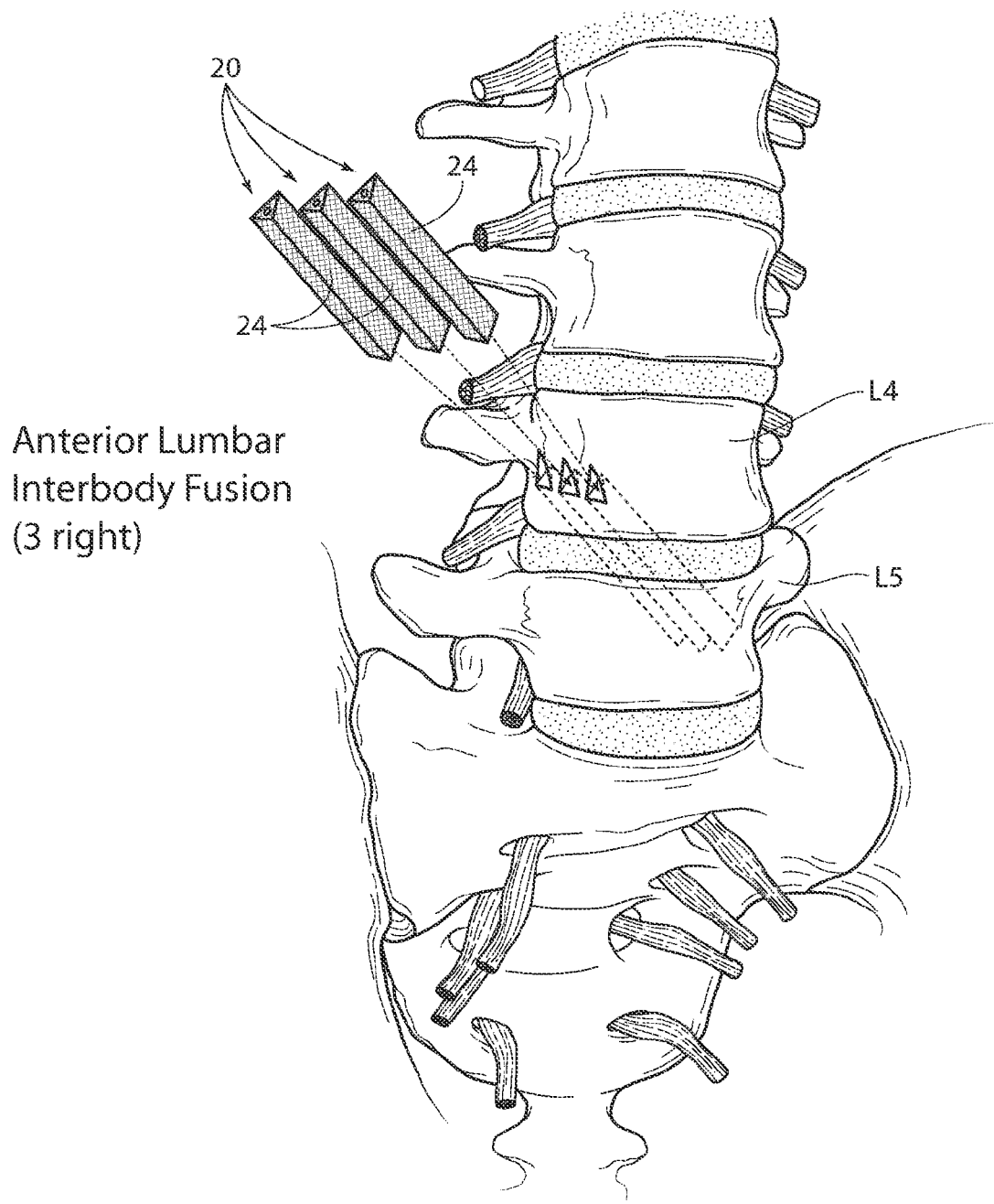
FIG. 9 is an anatomic anterior perspective view showing, in an exploded view prior to implantation, a representative configuration of an assembly of one or more implant structures as shown in FIG. 4, sized and configured to achieve anterior lumbar interbody fusion, in a non-invasive manner and without removal of the intervertebral disc.
Figure 10:
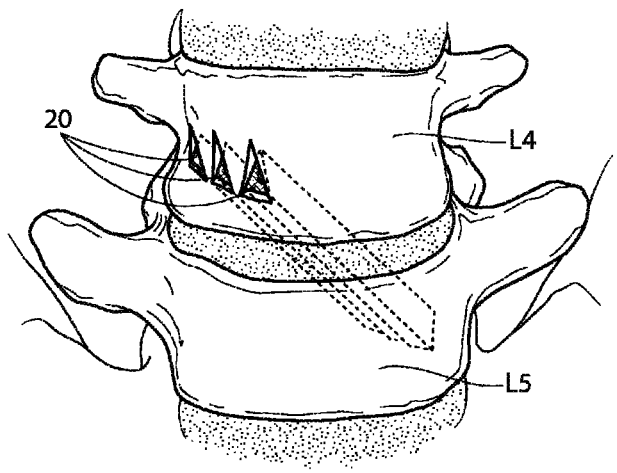
FIG. 10 is an anatomic anterior perspective view showing the assembly shown in FIG. 9 after implantation.
Figure 11:
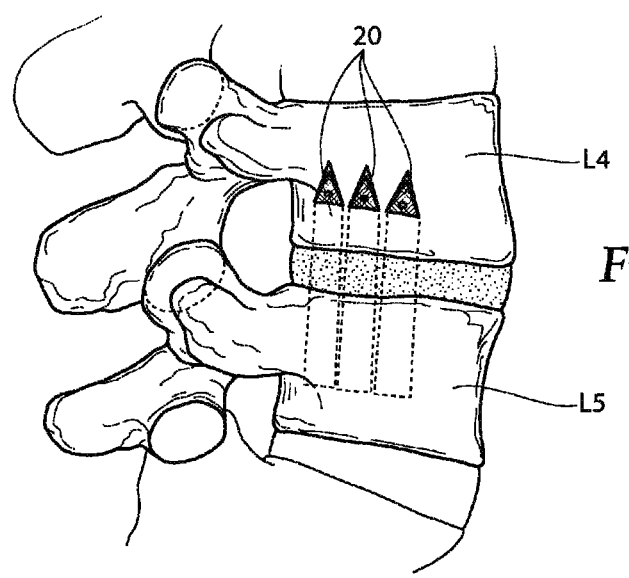
FIG. 11 is an anatomic right lateral perspective view showing the assembly shown in FIG. 9 after implantation.
Figure 12:
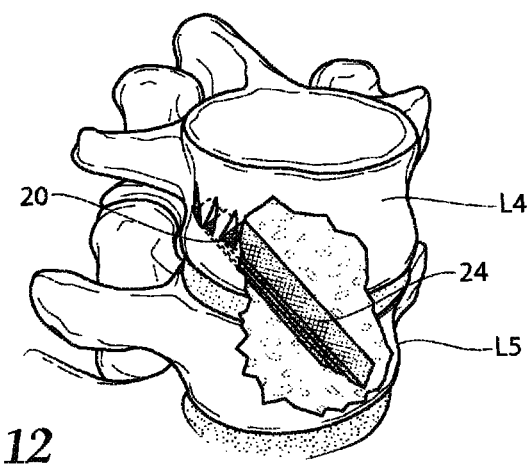
FIG. 12 is an anatomic superior left lateral perspective view showing the assembly shown in FIG. 9 after implantation.

FIG. 9 shows, in an exploded view prior to implantation, a representative configuration of an assembly of one or more implant structures 20 sized and configured to achieve anterior lumbar interbody fusion, in a non-invasive manner and without removal of the intervertebral disc. FIGS. 10 to 12 show the assembly after implantation, respectively, in an anterior view, a right lateral view, and a superior left lateral perspective view.

In the representative embodiment illustrated in FIGS. 10 to 12, the assembly comprises three implant structures 20. It should be appreciated, however, that a given assembly can include a greater or lesser number of implant structures 20.

In the representative embodiment shown in FIGS. 10 to 12, the three implant structures 20 are spaced in an adjacent lateral array. The implant structures 20 extend from an anterolateral region of a selected vertebral body (i.e., a lateral region anterior to a transverse process), across the intervertebral disc into an opposite anterolateral region of an adjacent caudal (inferior) vertebra. As shown in FIGS. 10 to 12, the array of implant structures 20 extends in an angled path (e.g., about 20° to about 40° off horizontal) through the cranial (superior) lumbar vertebral body (shown as L4) in an inferior direction, through the adjoining intervertebral disc, and terminates in the next adjacent caudal (inferior) lumbar vertebral body (shown as L5).

More particularly, in the representative embodiment shown in FIGS. 9 to 12, the implant structures 20 enter the right anterolateral region of vertebra L4 and terminate within the left anterolateral interior of vertebra L5, spanning the intervertebral disc between L4 and L5.

Alternatively, or in combination, an array of implant structures 20 can likewise extend between L5 and S1 in the same trans-disc formation.

The implant structures 20 are sized according to the local anatomy. The implant structures 20 can be sized differently, e.g., 3 mm, 4 mm, 6 mm, etc.), to accommodate anterolateral variations in the anatomy. The implant structures 20 can be sized for implantation in adults or children.

The intimate contact created between the bony in-growth or through-growth region 24 along the surface of the implant structure 20 accelerates bony in-growth or through-growth onto, into, or through the implant structure 20, to accelerate trans-disc fusion between these lumbar vertebrae.

FIGS. 13A to 13G diagrammatically show, for purposes of illustration, a representative lateral (or posterolateral) procedure for implanting the assembly of implant structures 20 shown in FIGS. 10 to 12.

The physician identifies the vertebrae of the lumbar spine region that are to be fused using, e.g., the Faber Test, or CT-guided injection, or X-ray/MRI of the lumbar spine. Aided by lateral and anterior-posterior (A-P) c-arms, and with the patient lying in a prone position (on their stomach), the physician makes a 3 mm incision laterally or posterolaterally from the side (see FIG. 13A). Aided by conventional visualization techniques, e.g., using X-ray image intensifiers such as a C-arms or fluoroscopes to produce a live image feed which is displayed on a TV screen, a guide pin 38 is introduced by conventional means into L4 (see FIG. 13B) for the first, most anterolateral implant structure (closest to the right transverse process of L4), in the desired angled inferiorly-directed path through the intervertebral disc and into the interior left anterolateral region of vertebra L5.

When the guide pin 38 is placed in the desired orientation, the physician desirable slides a soft tissue protector over the guide pin 38 before proceeding further. To simplify the illustration, the soft tissue protector is not shown in the drawings.

Figure 13A:
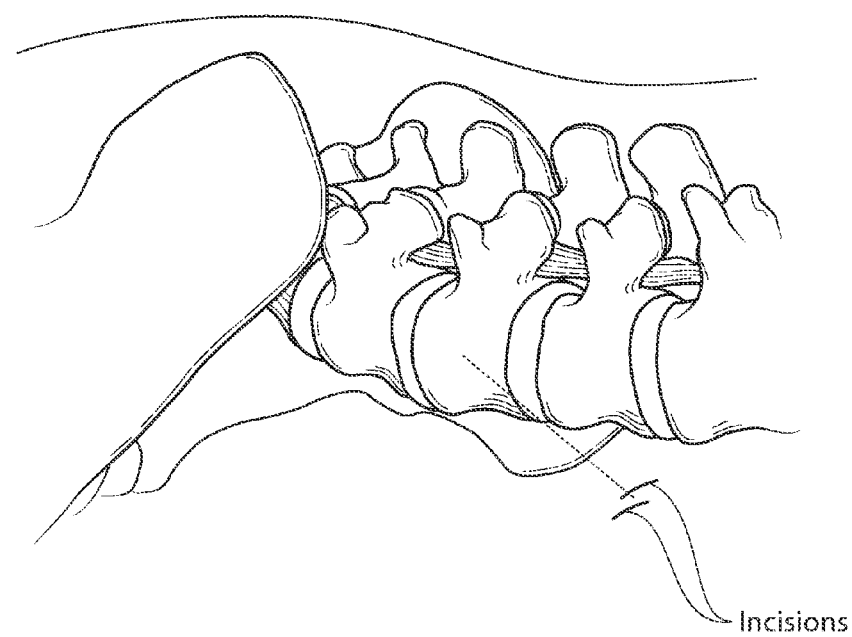
FIGS. 13A to 13G are diagrammatic views showing, for purposes of illustration, a representative lateral (or postero-lateral) procedure for implanting the assembly of implant structures shown in FIGS. 10 to 12.
Figure 13B:
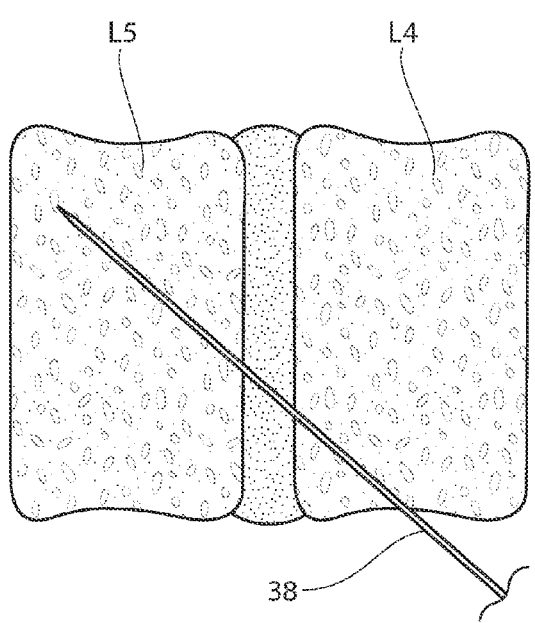
Figure 13C:
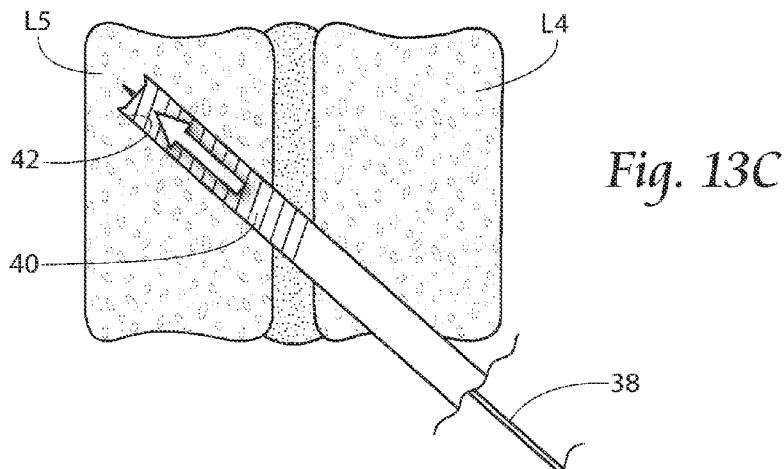
Figure 13D:
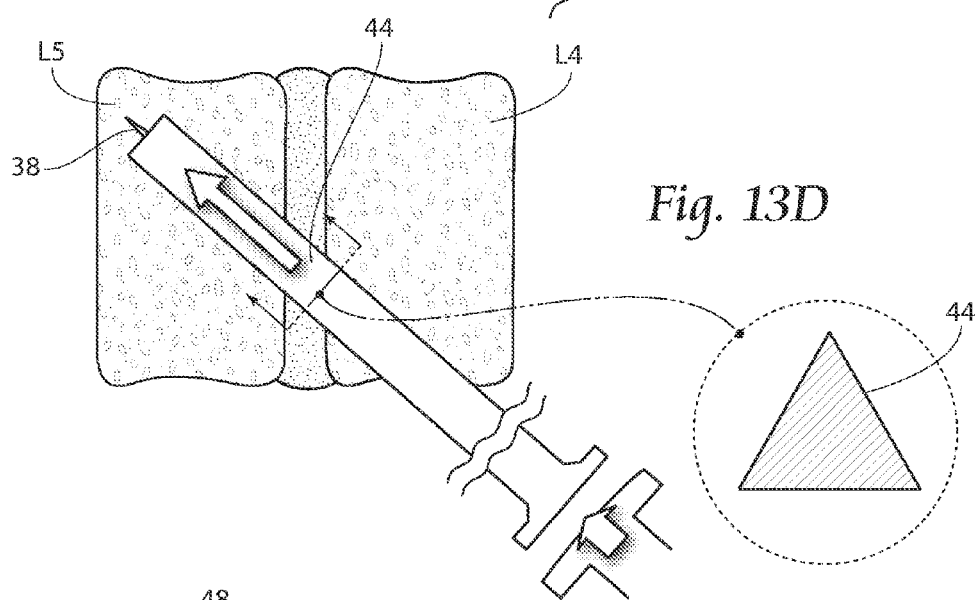
Figure 13E:
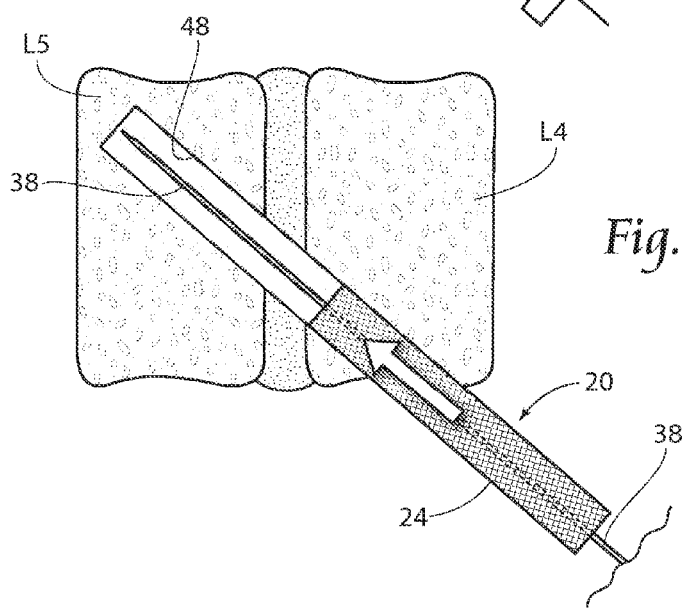

Through the soft tissue protector, a cannulated drill bit 40 is next passed over the guide pin 38 (see FIG. 13C). The cannulated drill bit 40 forms a pilot insertion path or bore 42 along the first angled path defined by the guide pin 38. A single drill bit or multiple drill bits 40 can be employed to drill through bone fragments or bone surfaces to create a pilot bore 42 of the desired size and configuration.

When the pilot bore 42 is completed, the cannulated drill bit 40 is withdrawn over the guide pin 38.

Through the soft tissue protector, a broach 44 having the external geometry and dimensions matching the external geometry and dimensions of the implant structure 20 (which, in the illustrated embodiment, is triangular) (see FIG. 13D) is tapped through the soft tissue protector over the guide pin 38 and into the pilot bore 42. The shaped broach 44 cuts along the edges of the pilot bore 42 to form the desired profile (which, in the illustrated embodiment, is triangular) to accommodate the implant structure 20.

The broach 44 is withdrawn (see FIG. 13E), and the first, most anterolateral implant structure 20 is passed over the guide pin 38 through the soft tissue protector into the broached bore 48. The guide pin 38 and soft tissue protector are withdrawn from the first implant structure 20.

Figure 13F:
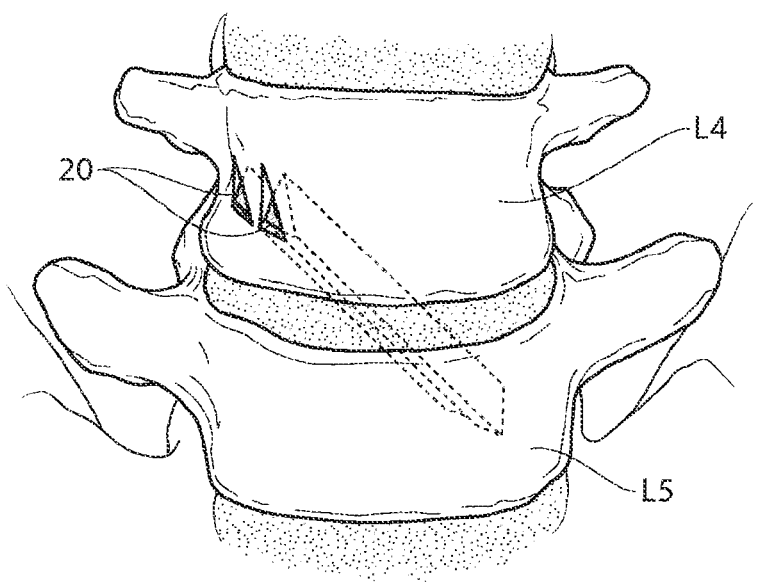
Figure 13G:
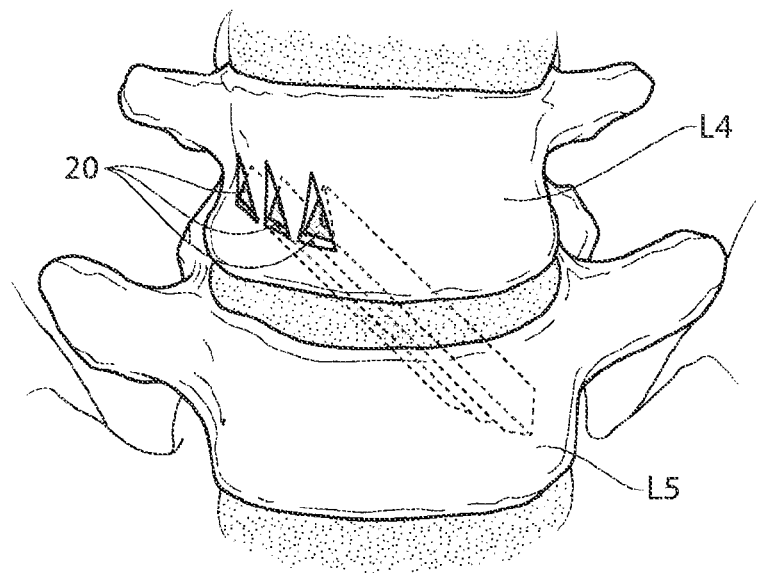

The physician repeats the above-described procedure sequentially for the next anterolateral implant structures 20: for each implant structure, inserting the guide pin 38, forming the pilot bore, forming the broached bore, inserting the respective implant structure, withdrawing the guide pin, and then repeating the procedure for the next implant structure, and so on until all implant structures 20 are placed (as FIGS. 13F and 13G indicate). The incision site(s) are closed.

In summary, the method for implanting the assembly of the implant structures 20 comprises (i) identifying the bone structures to be fused and/or stabilized; (ii) opening an incision; (iii) using a guide pin to established a desired implantation path through bone for the implant structure 20; (iv) guided by the guide pin, increasing the cross section of the path; (v) guided by the guide pin, shaping the cross section of the path to correspond with the cross section of the implant structure 20; (vi) inserting the implant structure 20 through the path over the guide pin; (vii) withdrawing the guide pin; (viii) repeating, as necessary, the procedure sequentially for the next implant structure(s) until all implant structures 20 contemplated are implanted; and (ix) closing the incision.

Figure 14:
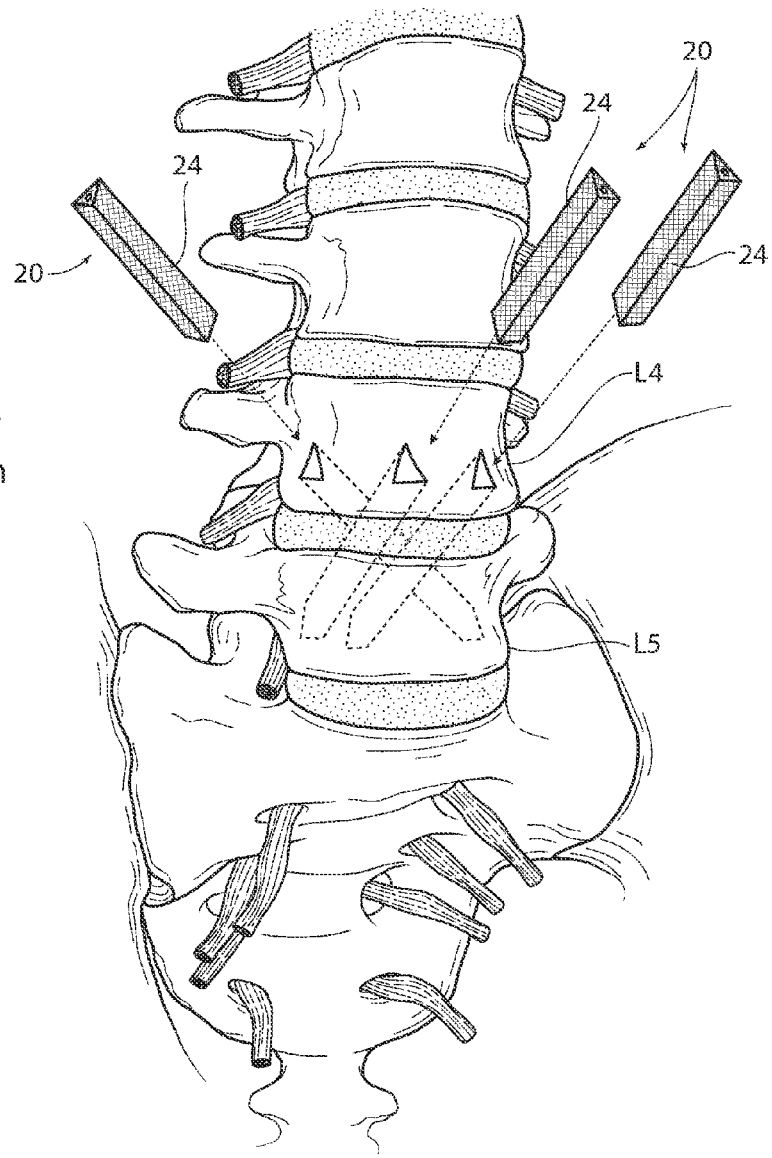
FIG. 14 is an anatomic anterior perspective view showing, in an exploded view prior to implantation, assemblies comprising one or more implant structures like that shown in FIG. 4 inserted from left and/or right anterolateral regions of a given lumbar vertebra, in an angled path through the intervertebral disc and into an opposite anterolateral interior region of the next inferior lumbar vertebra, FIG. 14 showing in particular two implant structures entering on the right anterolateral side of L4, through the intervertebral disc and into the left anterolateral region of L5, and one implant structure entering on the left anterolateral side of L4, through the intervertebral disc and into the right anterolateral region of L5, the left and right implant structures crossing each other in transit through the intervertebral disc.
Figure 15:
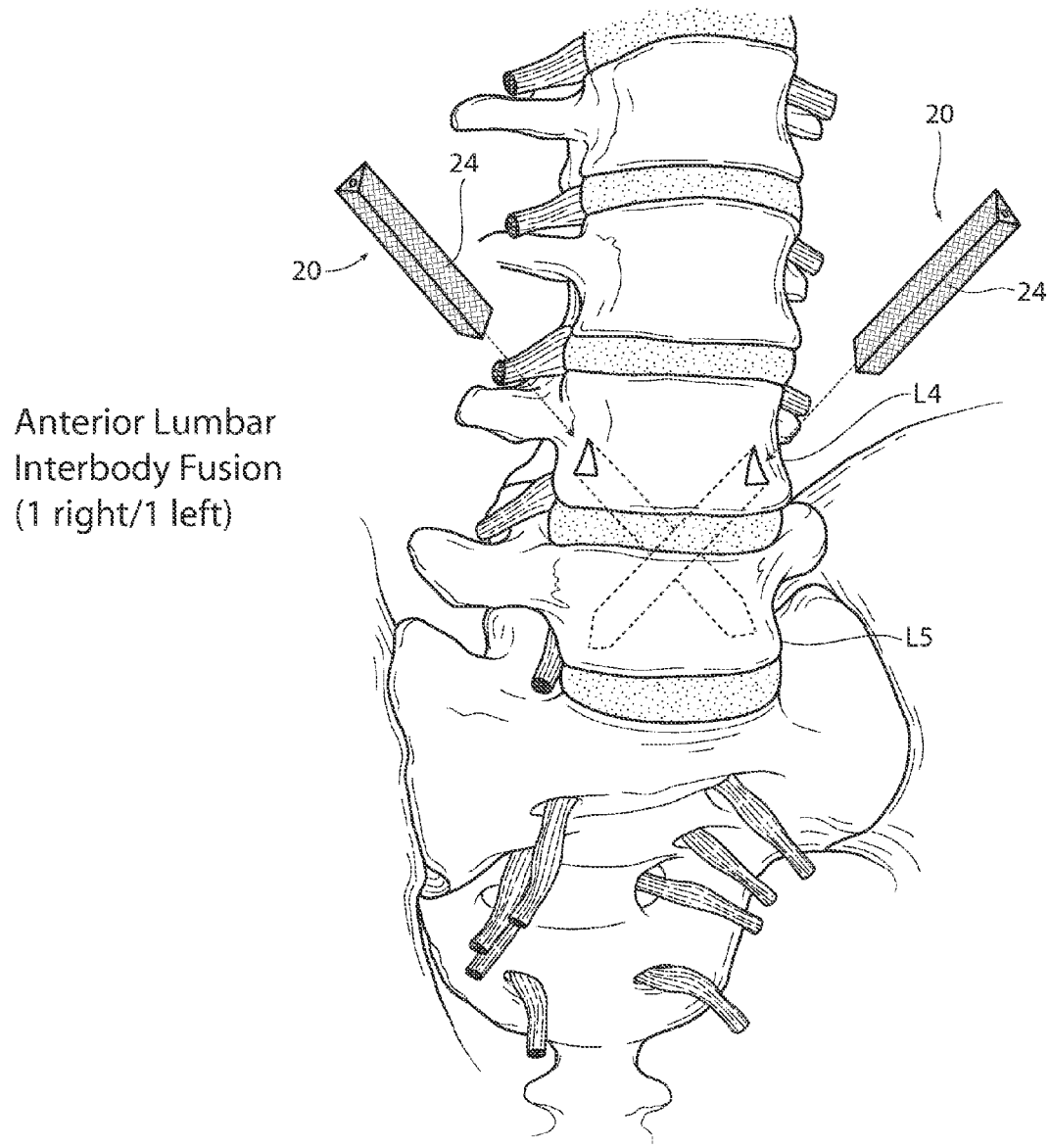
FIG. 15 is an anatomic anterior perspective view showing, in an exploded view prior to implantation, assemblies comprising one or more implant structures like that shown in FIG. 4 inserted from left and/or right anterolateral regions of a given lumbar vertebra, in an angled path through the intervertebral disc and into an opposite anterolateral interior region of the next inferior lumbar vertebra, FIG. 14 showing in particular one implant structure entering on the right anterolateral side of L4, through the intervertebral disc and into the left anterolateral region of L5, and one implant structure entering on the left anterolateral side of L4, through the intervertebral disc and into the right anterolateral region of L5, the left and right implant structures crossing each other in transit through the intervertebral disc.

As FIGS. 14 and 15 show, assemblies comprising one or more implant structures 20 can be inserted from left and/or right anterolateral regions of a given lumbar vertebra, in an angled path through the intervertebral disc and into an opposite anterolateral interior region of the next inferior lumbar vertebra.

For purposes of illustration, FIG. 14 shows two implant structures 20 entering on the right anterolateral side of L4, through the intervertebral disc and into the left anterolateral region of L5, and one implant structure 20 entering on the left anterolateral side of L4, through the intervertebral disc and into the right anterolateral region of L5. In this arrangement, the left and right implant structures 20 cross each other in transit through the intervertebral disc.

As another illustration of a representative embodiment, FIG. 15 shows one implant structure 20 entering on the right anterolateral side of L4, through the intervertebral disc and into the left anterolateral region of L5, and one implant structure 20 entering on the left anterolateral side of L4, through the intervertebral disc and into the right anterolateral region of L5. In this arrangement as well, the left and right implant structures 20 cross each other in transit through the intervertebral disc.

B. Use of Implant Structures to Achieve Translaminal Lumbar Fusion (Posterior Approach)

Figure 16:
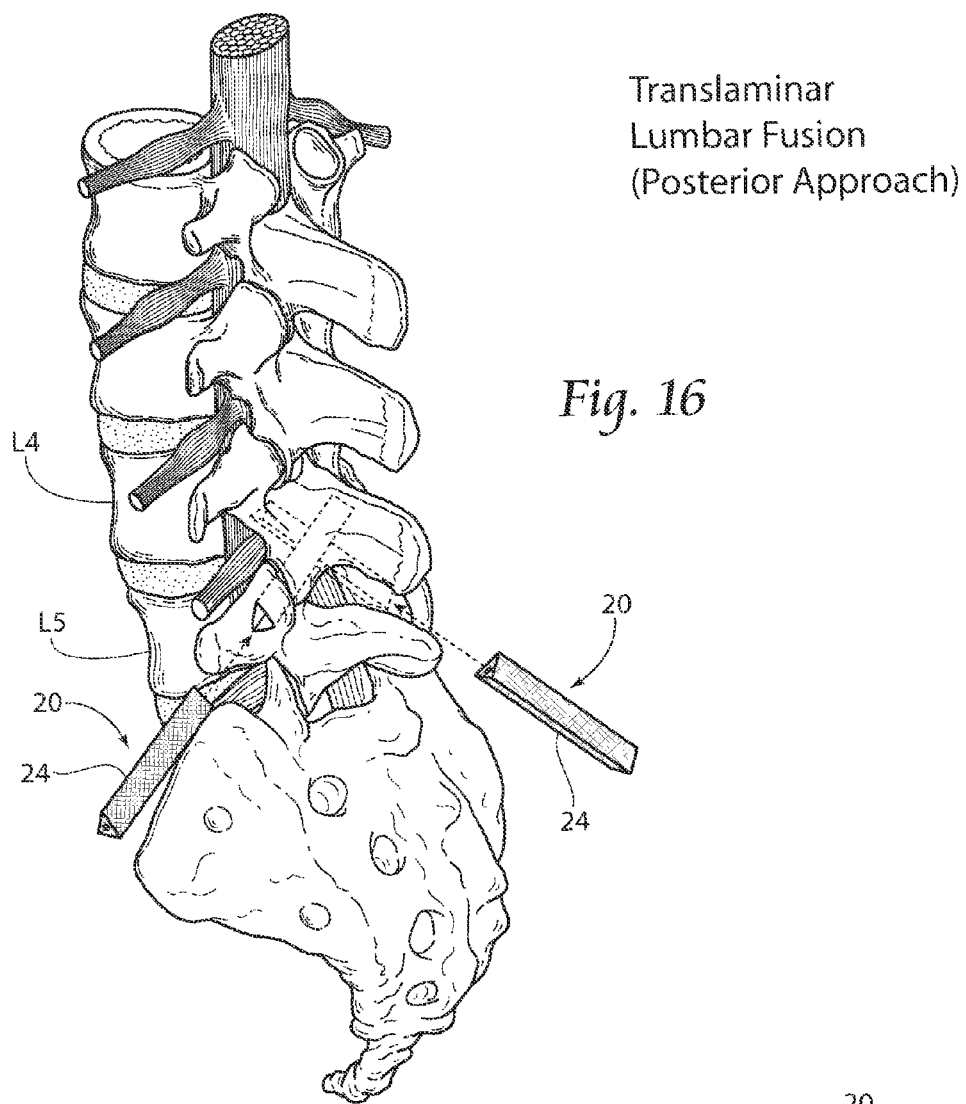
FIG. 16 is an anatomic posterior perspective view, exploded prior to implantation, of a representative configuration of an assembly of one or more implant structures like that shown in FIG. 4, sized and configured to achieve translaminar lumbar fusion in a non-invasive manner and without removal of the intervertebral disc.
Figure 17:
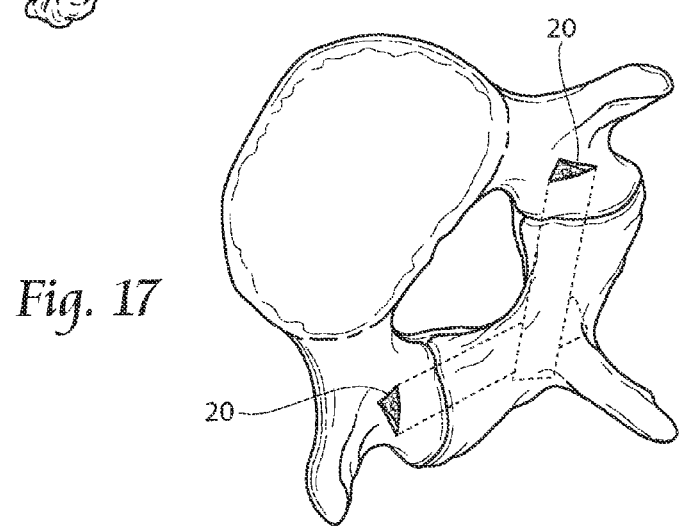
FIG. 17 is an anatomic inferior transverse plane view showing the assembly shown in FIG. 16 after implantation.

FIG. 16 shows, in an exploded view prior to implantation, a representative configuration of an assembly of one or more implant structures 20 sized and configured to achieve translaminar lumbar fusion in a non-invasive manner and without removal of the intervertebral disc. FIG. 17 shows the assembly after implantation, respectively, in an inferior transverse plane view.

As can be seen in the representative embodiment illustrated in FIGS. 16 and 17, the assembly comprises two implant structures 20. The first implant structure 20 extends from the left superior articular process of vertebra L5, through the adjoining facet capsule into the left inferior articular process of vertebra L4, and, from there, further through the lamina of vertebra L4 into an interior right posterolateral region of vertebra L4 adjacent the spinous process. The second implant structure 20 extends from the right superior articular process of vertebra L5, through the adjoining facet capsule into the right inferior articular process of vertebra L4, and, from there, further through the lamina of vertebra L4 into an interior left posterolateral region of vertebra L4 adjacent the spinous process. The first and second implant structures 20 cross each other within the medial lamina of vertebra L4.

The first and second implant structures 20 are sized and configured according to the local anatomy. The selection of a translaminar lumbar fusion (posterior approach) is indicated when the facet joints are aligned with the sagittal plane. Removal of the intervertebral disc is not required, unless the condition of the disc warrants its removal.

A procedure incorporating the technical features of the procedure shown in FIGS. 13A to 13G can be tailored to a posterior procedure for implanting the assembly of implant structures 20 shown in FIGS. 16 and 17. The method comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to established a desired implantation path through bone for the first (e.g., left side) implant structure 20, which, in FIGS. 16 and 17, traverses through the left superior articular process of vertebra L5, through the adjoining facet capsule into the left inferior articular process of vertebra L4, and then through the lamina of vertebra L4 into an interior right posterolateral region of vertebra L4 adjacent the spinous process. The method further includes (iv) guided by the guide pin, increasing the cross section of the path; (v) guided by the guide pin, shaping the cross section of the path to correspond with the cross section of the implant structure; (vi) inserting the implant structure 20 through the path over the guide pin; (vii) withdrawing the guide pin; and (viii) using a guide pin to established a desired implantation path through bone for the second (e.g., right side) implant structure 20, which, in FIGS. 16 and 17, traverses through the right superior articular process of vertebra L5, through the adjoining facet capsule into the right inferior articular process of vertebra L4, and through the lamina of vertebra L4 into an interior left posterolateral region of vertebra L4 adjacent the spinous process. The physician repeats the remainder of the above-described procedure sequentially for the right implant structure 20 as for the left, and, after withdrawing the guide pin, closes the incision.

The intimate contact created between the bony in-growth or through-growth region 24 along the surface of the implant structure 20 across the facet joint accelerates bony in-growth or through-growth onto, into, or through the implant structure 20, to accelerate fusion of the facets joints between L4 and L5. Of course, translaminar lumbar fusion between L5 and S1 can be achieved using first and second implant structures in the same manner.

C. Use of Implant Structures to Achieve Lumbar Facet Fusion (Posterior Approach)

Figure 18:
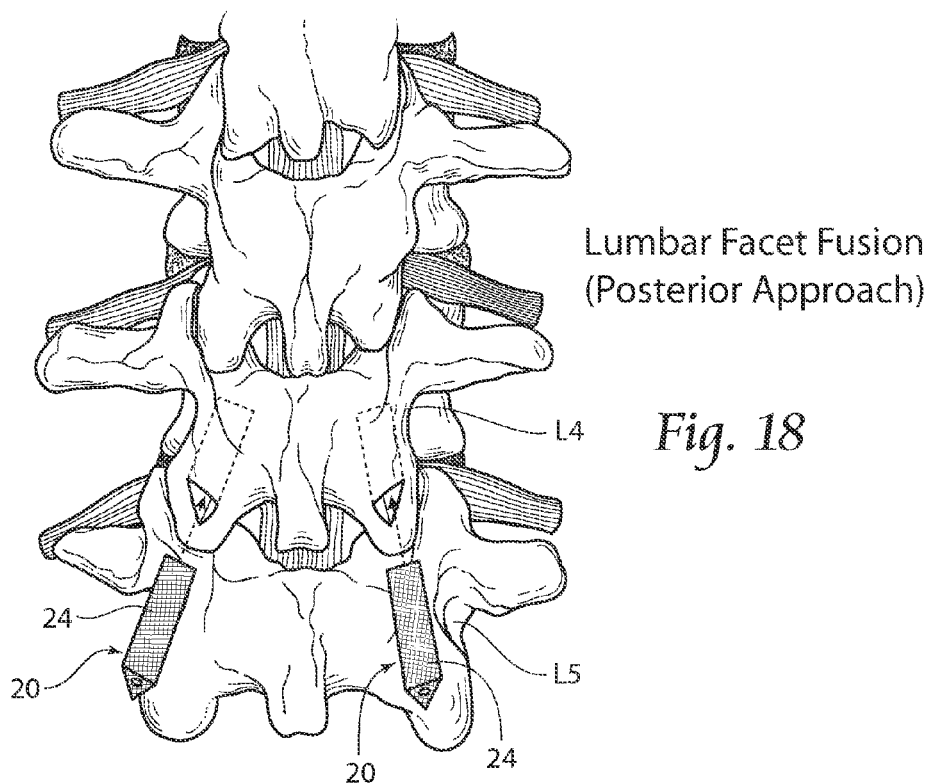
FIG. 18 is an anatomic posterior perspective view, exploded prior to implantation, of a representative configuration of an assembly of one or more implant structures like that shown in FIG. 4, sized and configured to achieve lumbar facet fusion, in a non-invasive manner and without removal of the intervertebral disc.
Figure 19:
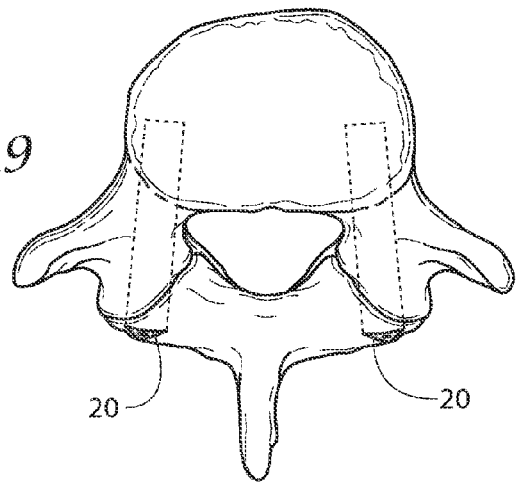
FIG. 19 is an anatomic inferior transverse plane view showing the assembly shown in FIG. 18 after implantation.
Figure 20:
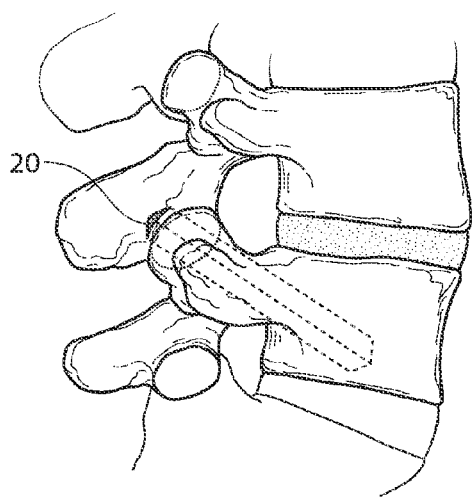
FIG. 20 is an anatomic lateral view showing the assembly shown in FIG. 18 after implantation.

FIG. 18 shows, in an exploded view prior to implantation, a representative configuration of an assembly of one or more implant structures 20 sized and configured to lumbar facet fusion, in a non-invasive manner and without removal of the intervertebral disc. FIGS. 19 and 20 show the assembly after implantation, respectively, in an inferior transverse plane view and a lateral view.

As can be seen in the representative embodiment illustrated in FIGS. 18 and 20, the assembly comprises two implant structures 20. The first implant structure 20 extends from the left inferior articular process of vertebra L4, through the adjoining facet capsule into the left superior articular process of vertebra L5 and into the pedicle of vertebra L5. The second implant structure 20 extends from the right inferior articular process of vertebra L5, through the adjoining facet capsule into the right superior articular process of vertebra L5 and into the pedicle of vertebra L5. In this arrangement, the first and second implant structures 20 extend in parallel directions on the left and right pedicles of vertebra L5. The first and second implant structures 20 are sized and configured according to the local anatomy. The selection of lumbar facet fusion (posterior approach) is indicated when the facet joints are coronally angled. Removal of the intervertebral disc is not necessary, unless the condition of the disc warrants its removal.

A procedure incorporating the technical features of the procedure shown in FIGS. 13A to 13G can be tailored to a posterior procedure for implanting the assembly of implant structures 20 shown in FIGS. 18 to 20. The method comprises (i) identifying the vertebrae of the lumbar spine region that are to be fused; (ii) opening an incision, which comprises, e.g., with the patient lying in a prone position (on their stomach), making a 3 mm posterior incision; and (iii) using a guide pin to established a desired implantation path through bone for the first (e.g., left side) implant structure 20, which, in FIGS. 18 to 20, traverses through the left inferior articular process of vertebra L4, through the adjoining facet capsule into the left superior articular process of vertebra L5 and into the pedicle of vertebra L5. The method further includes (iv) guided by the guide pin, increasing the cross section of the path; (v) guided by the guide pin, shaping the cross section of the path to correspond with the cross section of the implant structure 20; (vi) inserting the implant structure 20 through the path over the guide pin; (vii) withdrawing the guide pin; and (viii) using a guide pin to established a desired implantation path through bone for the second (e.g., right side) implant structure 20, which, in FIGS. 18 to 20, traverses through the right inferior articular process of vertebra L5, through the adjoining facet capsule into the right superior articular process of vertebra L5 and into the pedicle of vertebra L5. The physician repeats the remainder of the above-described procedure sequentially for the right implant structure 20 as for the left and, withdrawing the guide pin, closes the incision.

The intimate contact created between the bony in-growth or through-growth region 24 along the surface of the implant structure 20 across the facet joint accelerates bony in-growth or through-growth onto, into, or through the implant structure 20, to accelerate fusion of the facets joints between L4 and L5.

Of course, translaminar lumbar fusion between L5 and S1 can be achieved using first and second implant structures in the same manner.

D. Use of Implant Structures to Achieve Trans-Iliac Lumbar Fusion (Anterior Approach)

Figure 21A:
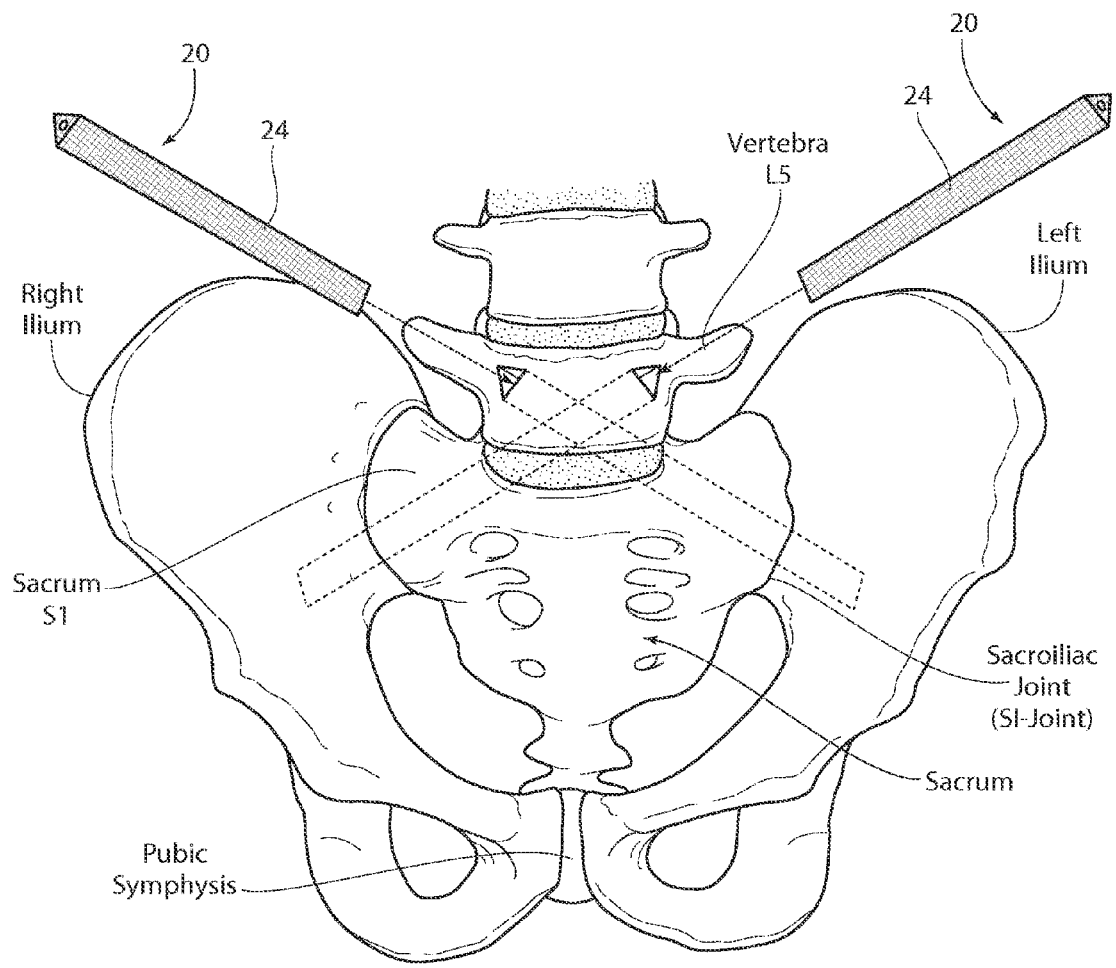
FIG. 21A is an anatomic anterior perspective view showing, in an exploded view prior to implantation, a representative configuration of an assembly of one or more implant structures like that shown in FIG. 4, sized and configured to achieve fusion between lumbar vertebra L5 and sacral vertebra S1, in a non-invasive manner and without removal of the intervertebral disc, using an anterior approach.
Figure 21B:
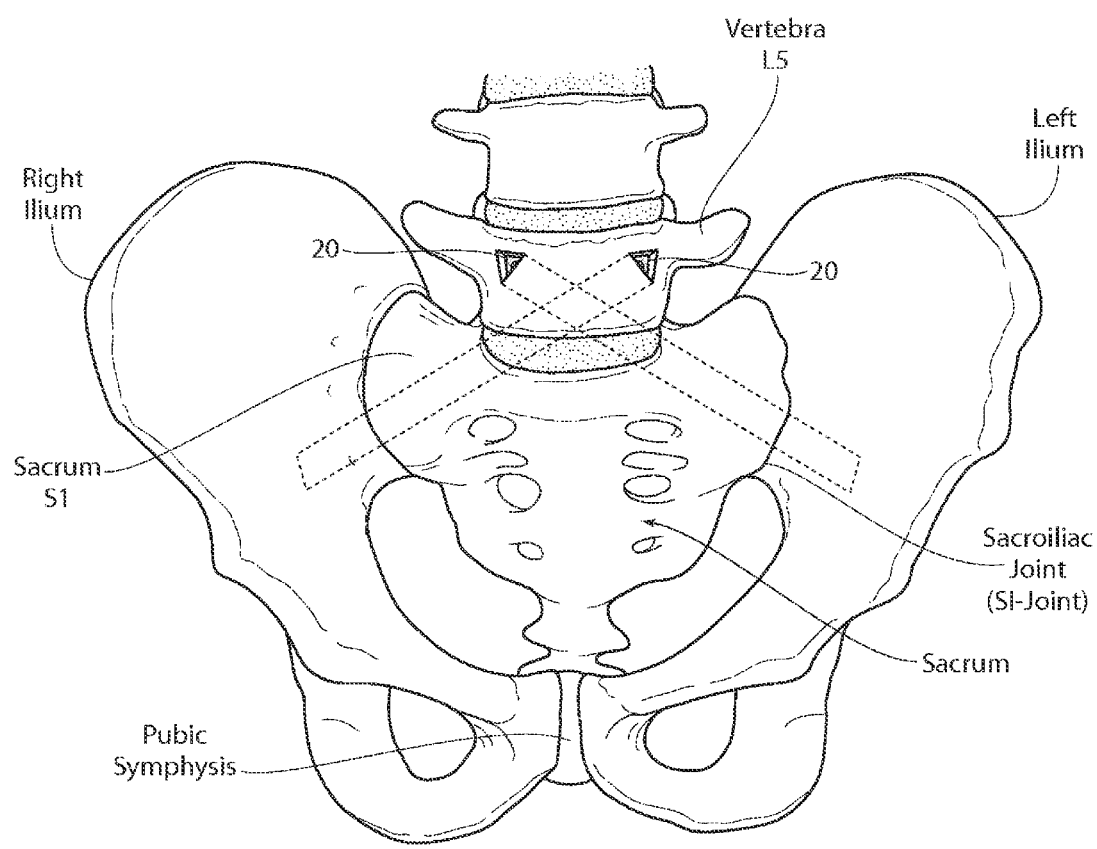
FIG. 21B is an anatomic anterior perspective view showing the assembly shown in FIG. 21A after implantation.

FIG. 21A shows, in an exploded view prior to implantation, a representative configuration of an assembly of one or more implant structures 20 sized and configured to achieve fusion between lumbar vertebra L5 and sacral vertebra S1, in a non-invasive manner and without removal of the intervertebral disc. FIG. 21B shows the assembly after implantation.

In the representative embodiment illustrated in FIGS. 21A and 21B, the assembly comprises two implant structures 20. It should be appreciated, however, that a given assembly can include a greater or lesser number of implant structures 20.

As FIGS. 21A and 21B show, the assembly comprises two implant structures 20 inserted from left and right anterolateral regions of lumbar vertebra L5, in an angled path (e.g., about 20° to about 40° off horizontal) through the intervertebral disc in an inferior direction, into and through opposite anterolateral interior regions of sacral vertebra S1, through the sacro-iliac joint, and terminating in the ilium. In this arrangement, the left and right implant structures 20 cross each other in transit through the intervertebral disc. As before described, the implant structures 20 are sized according to the local anatomy.

The intimate contact created between the bony in-growth or through-growth region 24 along the surface of the implant structure 20 accelerates bony in-growth or through-growth onto, into, or through the implant structure 20, to accelerate lumbar trans-iliac fusion between vertebra L5 and S1.

A physician can employ the lateral (or posterolateral) procedure as generally shown in FIGS. 13A to 13G for implanting the assembly of implant structures 20 shown in FIGS. 21A and 21B, including forming a pilot bore over a guide pin inserted in the angled path, forming a broached bore, inserting the right implant 20 structure, withdrawing the guide pin, and repeating for the left implant structure 20, or vice versa. The incision site(s) are closed.

The assembly as described makes possible the achievement of trans-iliac lumbar fusion using an anterior in a non-invasive manner, with minimal incision, and without necessarily removing the intervertebral disc between L5 and S1.

E. Use of Implant Structures to Achieve Trans-Iliac Lumbar Fusion (Postero-Lateral Approach From Posterior Iliac Spine)

Figure 22A:
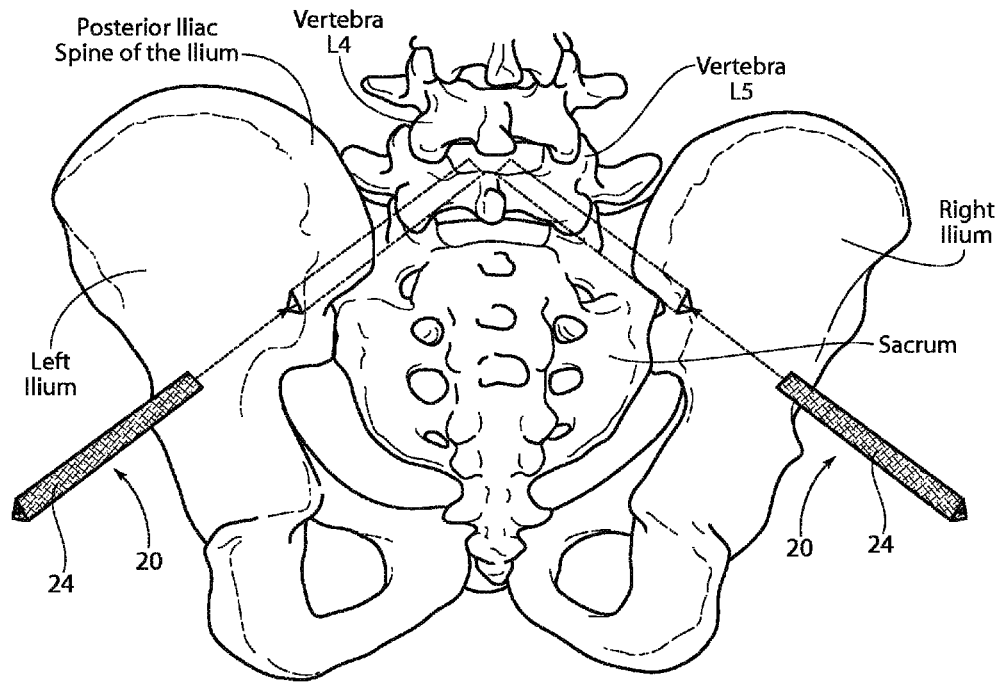
FIG. 22A is an anatomic posterior view showing, in an exploded view prior to implantation, another representative configuration of an assembly of one or more implant structures 20 sized and configured to achieve fusion between lumbar vertebra L5 and sacral vertebra S1, in a non-invasive manner and without removal of the intervertebral disc, using a postero-lateral approach entering from the posterior iliac spine of the ilium, angling through the SI-Joint, and terminating in the lumbar vertebra L5.
Figure 22B:
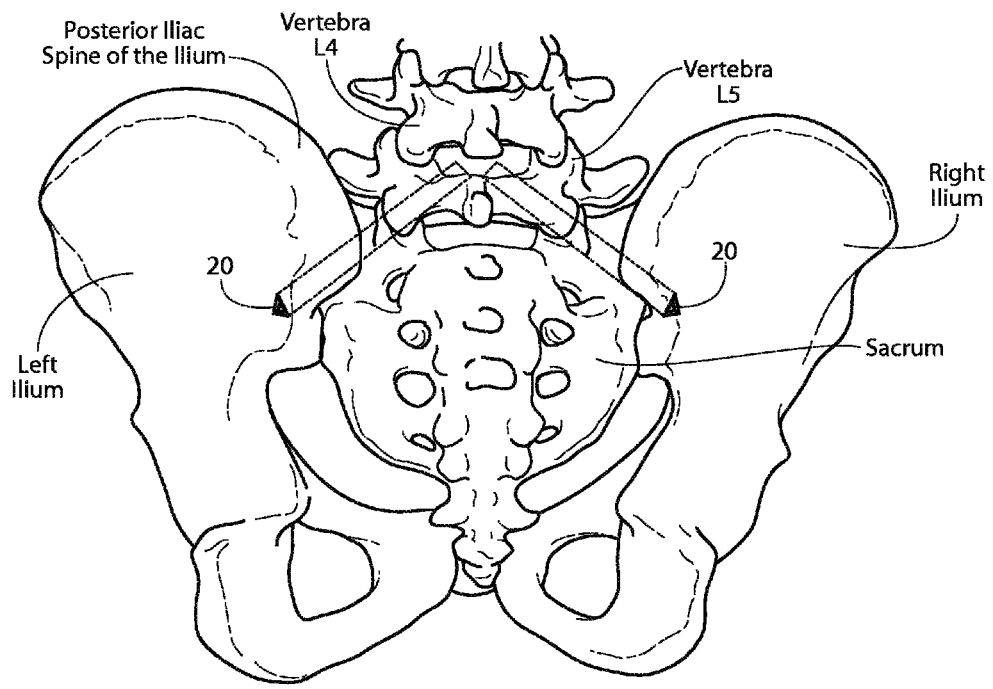
FIG. 22B is an anatomic posterior view showing the assembly shown in FIG. 22A after implantation.
Figure 22C:
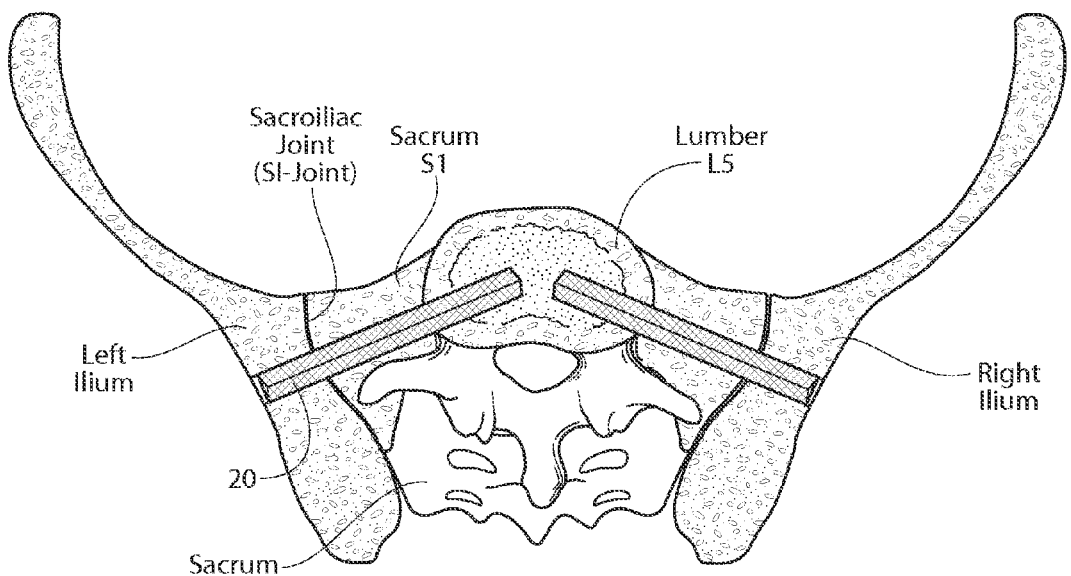
FIG. 22C is an anatomic superior view showing the assembly shown in FIG. 22B.

FIG. 22A shows, in an exploded view prior to implantation, another representative configuration of an assembly of one or more implant structures 20 sized and configured to achieve fusion between lumbar vertebra L5 and sacral vertebra S1, in a non-invasive manner and without removal of the intervertebral disc. FIGS. 22B and 22C show the assembly after implantation.

As FIGS. 22A and 22B show, the one or more implant structures are introduced in a postero-lateral approach entering from the posterior iliac spine of the ilium, angling through the SI-Joint into and through the sacral vertebra S1, and terminating in the lumbar vertebra L5. This path and resulting placement of the implant structures 20 are also shown in FIG. 22C. In the illustrated embodiment, two implant structures 20 are placed in this manner, but there can be more or fewer implant structures 20. Also in the illustrated embodiment, the implant structures 20 are triangular in cross section, but it should be appreciated that implant structures 20 of other cross sections as previously described can be used.

The postero-lateral approach involves less soft tissue disruption that the lateral approach, because there is less soft tissue overlying the entry point of the posterior iliac spine of the ilium. Introduction of the implant structure 20 from this region therefore makes possible a smaller, more mobile incision.

The set-up for a postero-lateral approach is generally the same as for a lateral approach. It desirably involves the identification of the lumbar region that is to be fixated or fused (arthrodesed) using, e.g., the Faber Test, or CT-guided injection, or X-ray/MRI of SI Joint. It is desirable performed with the patient lying in a prone position (on their stomach) and is aided by lateral and anterior-posterior (A-P) c-arms. The same surgical tools are used to form the pilot bore over a guide pin (e.g., on the right side), except the path of the pilot bore now starts from the posterior iliac spine of the ilium, angles through the SI-Joint, and terminates in the lumbar vertebra L5. The broached bore is formed, and the right implant 20 structure is inserted. The guide pin is withdrawn, and the procedure is repeated for the left implant structure 20, or vice versa. The incision site(s) are closed.

The assembly as described makes possible the achievement of trans-iliac lumbar fusion using a postero-lateral approach in a non-invasive manner, with minimal incision, and without necessarily removing the intervertebral disc between L5 and S1.

F. Use of Implant Structures to Stabilize a Spondylolisthesis

Figure 23:
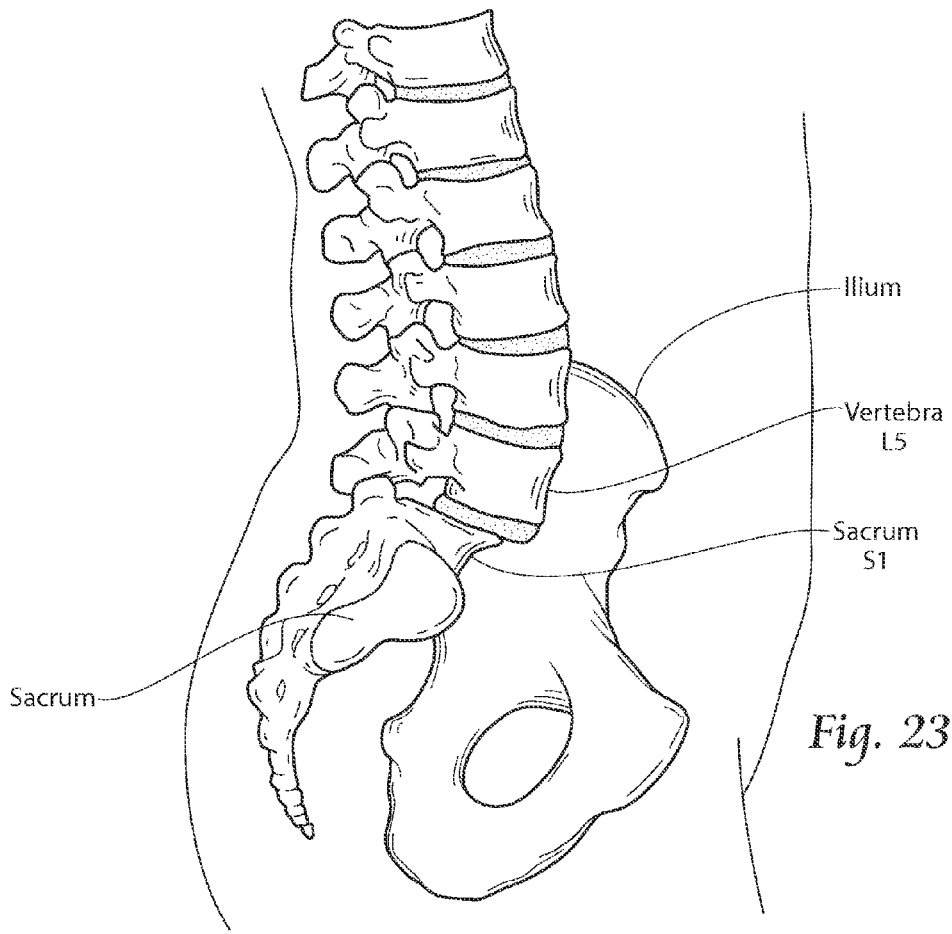
FIG. 23 is an anatomic laterial view showing a spondylolisthesis at the L5/S1 articulation, in which the lumbar vertebra L5 is displaced forward (anterior) of the sacral vertebra S1.

FIG. 23 shows a spondylolisthesis at the L5/S1 articulation, in which the lumbar vertebra L5 is displaced forward (anterior) of the sacral vertebra S1. As FIG. 23 shows, the posterior fragment of L5 remains in normal relation to the sacrum, but the anterior fragment and the L5 vertebral body has moved anteriorly. Spondylolisthesis at the L5/S1 articulation can result in pressure in the spinal nerves of the cauda equine as they pass into the superior part of the sacrum, causing back and lower limb pain.

Figure 24A:
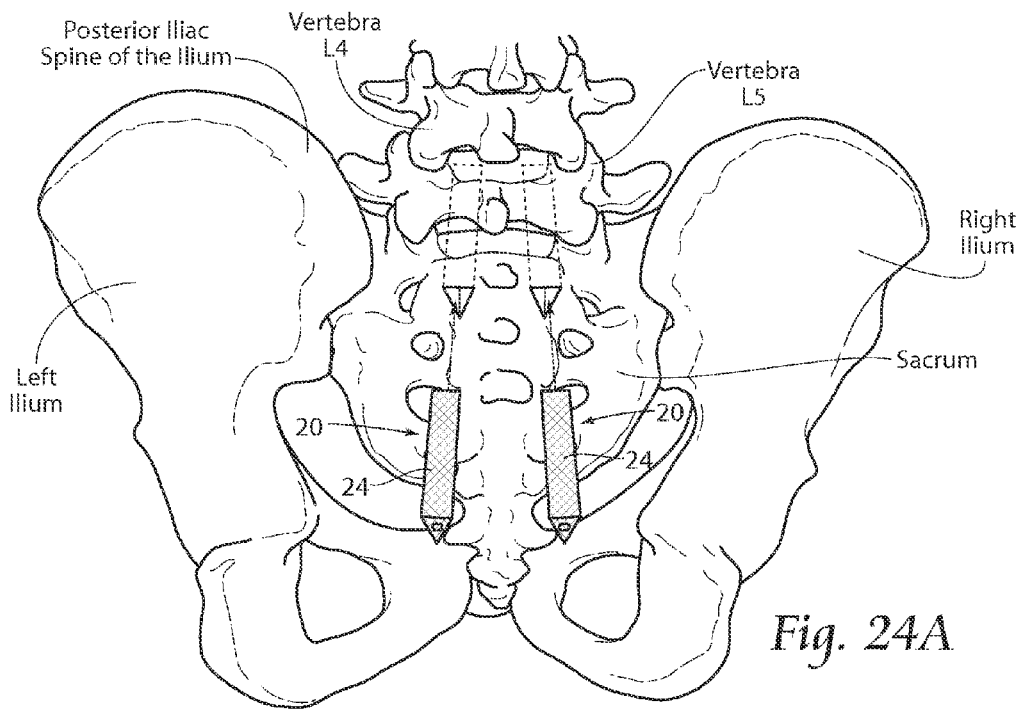
FIG. 24A is an anatomic anterior perspective view showing, in an exploded view prior to implantation, a representative configuration of an assembly of one or more implant structures like that shown in FIG. 4, sized and configured to stabilize a spondylolisthesis at the L5/S1 articulation.
Figure 24B:
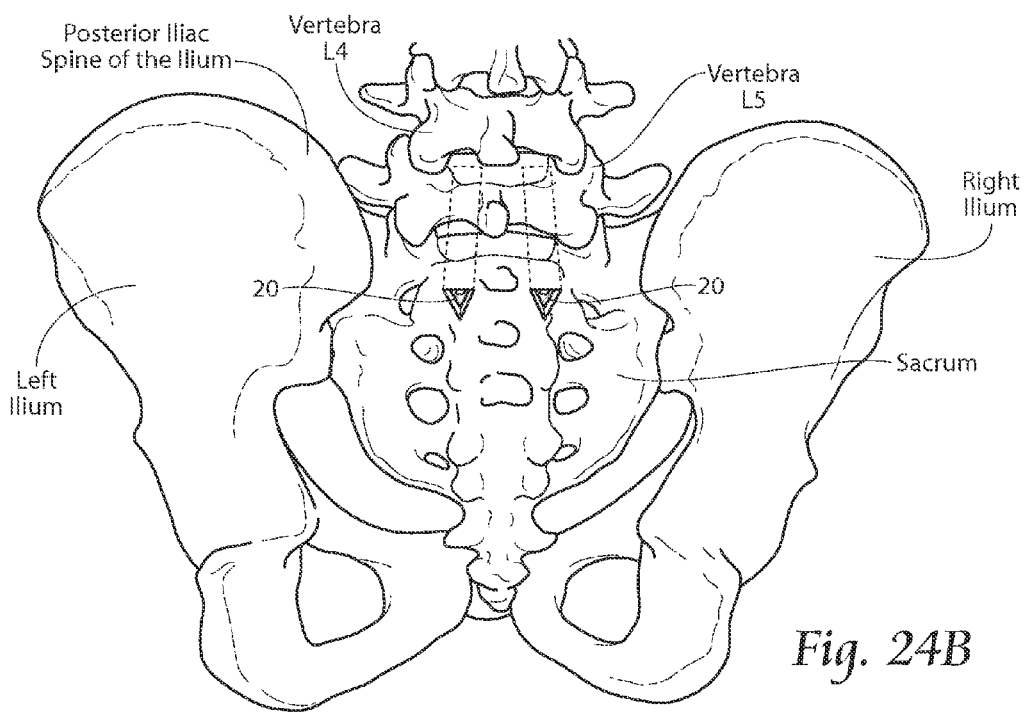
FIG. 24B is an anatomic anterior perspective view showing the assembly shown in FIG. 24A after implantation.
Figure 24C:
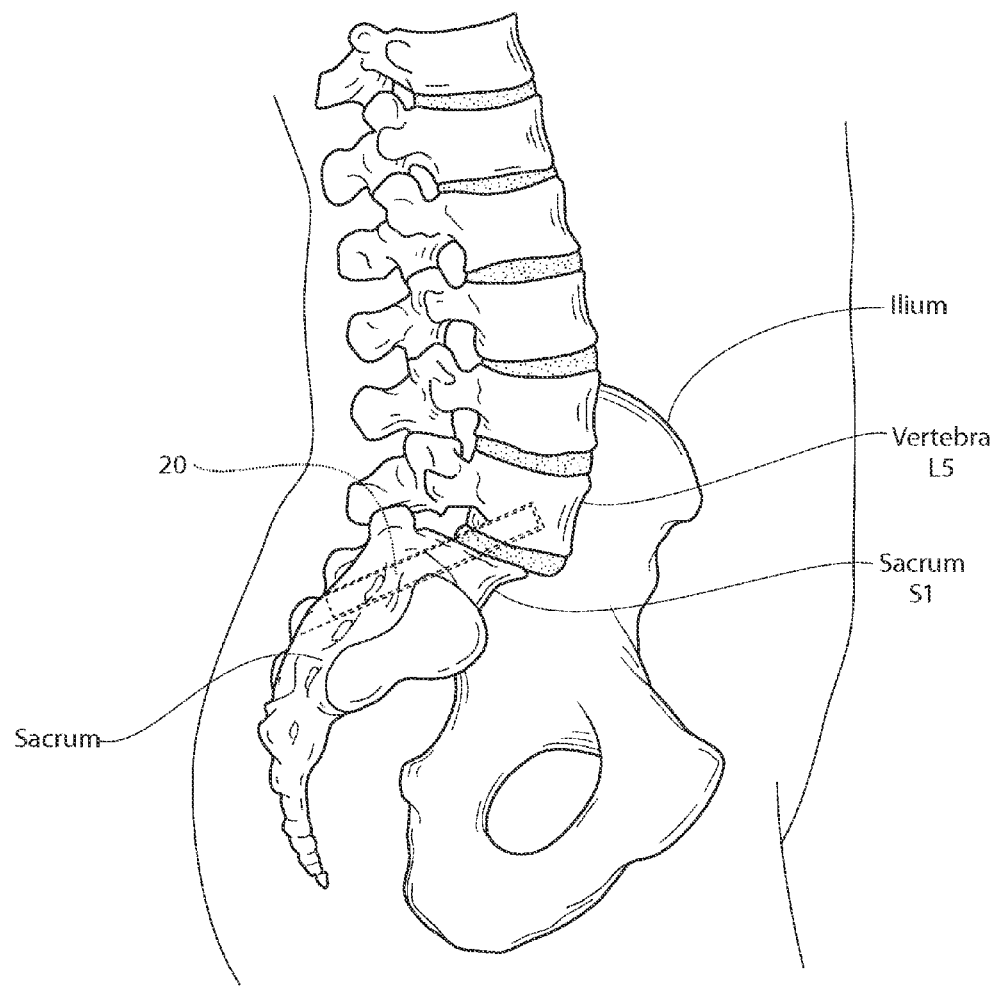
FIG. 24C is an anatomic lateral view showing the assembly shown in FIG. 24B.
Figure 2:
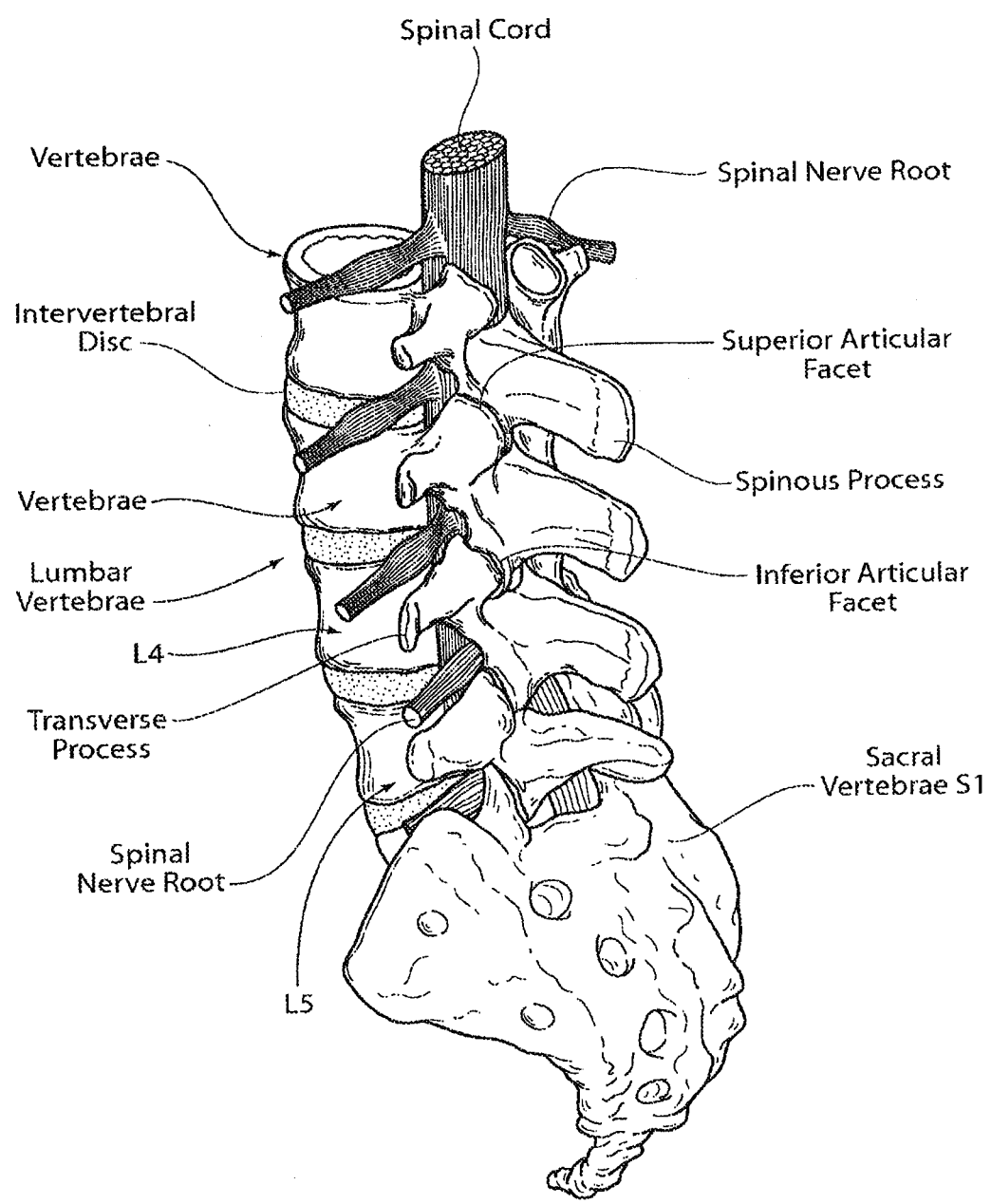

FIG. 24A shows, in an exploded view prior to implantation, a representative configuration of an assembly of one or more implant structures 20 sized and configured to stabilize the spondylolisthesis at the L5/S1 articulation. FIGS. 24B and 24C show the assembly after implantation.

As shown, the implant structure 20 extends from a posterolateral region of the sacral vertebra S1, across the intervertebral disc into an opposite anterolateral region of the lumbar vertebra L5. The implant structure 20 extends in an angled path (e.g., about 20° to about 40° off horizontal) through the sacral vertebra S1 in a superior direction, through the adjoining intervertebral disc, and terminates in the lumbar vertebra L5.

A physician can employ a posterior approach for implanting the implant structure 20 shown in FIGS. 24A, 24B, and 24C, which includes forming a pilot bore over a guide pin inserted in the angled path from the posterior of the sacral vertebra S1 through the intervertebral disc and into an opposite anterolateral region of the lumbar vertebra L5, forming a broached bore, inserting the implant structure 20, and withdrawing the guide pin. The incision site is then closed. As previously described, more than one implant structure 20 can be placed in the same manner to stabilize a spondylolisthesis. Furthermore, a physician can fixate the implant structure(s) 20 using the anterior trans-iliac lumbar path, as shown in FIG. 21A/B or 22A/B/C.

The physician can, if desired, combine stabilization of the spondylolisthesis, as shown in FIG. 24A/B/C, with a reduction, realigning L5 and S-1. The physician can also, if desired, combine stabilization of the spondylolisthesis, as shown in FIG. 24A/B/C (with or without reduction of the spondylolisthesis), with a lumbar facet fusion, as shown in FIGS. 18 to 20. The physician can also, if desired, combine stabilization of the spondylolisthesis, as shown in FIG. 24A/B/C, with a decompression, e.g., by the posterior removal of the spinous process and laminae bilaterally.

II. Conclusion

The various representative embodiments of the assemblies of the implant structures 20, as described, make possible the achievement of diverse interventions involving the fusion and/or stabilization of lumbar and sacral vertebra in a non-invasive manner, with minimal incision, and without the necessitating the removing the intervertebral disc. The representative lumbar spine interventions described can be performed on adults or children and include, but are not limited to, lumbar interbody fusion; translaminar lumbar fusion; lumbar facet fusion; trans-iliac lumbar fusion; and the stabilization of a spondylolisthesis. It should be appreciated that such interventions can be used in combination with each other and in combination with conventional fusion/fixation techniques to achieve the desired therapeutic objectives.

Significantly, the various assemblies of the implant structures 20 as described make possible lumbar interbody fusion without the necessity of removing the intervertebral disc. For example, in conventional anterior lumbar interbody fusion procedures, the removal of the intervertebral disc is a prerequisite of the procedure. However, when using the assemblies as described to achieve anterior lumbar interbody fusion, whether or not the intervertebral disc is removed depends upon the condition of the disc, and is not a prerequisite of the procedure itself. If the disc is healthy and has not appreciably degenerated, one or more implant structures 20 can be individually inserted in a minimally invasive fashion, across the intervertebral disc in the lumbar spine area, leaving the disc intact.

In all the representative interventions described, the removal of a disc, or the scraping of a disc, is at the physician's discretion, based upon the condition of the disc itself, and is not dictated by the procedure. The bony in-growth or through-growth regions 24 of the implant structures 20 described provide both extra-articular and intra osseous fixation, when bone grows in and around the bony in-growth or through-growth regions 24.

Conventional tissue access tools, obturators, cannulas, and/or drills can be used during their implantation. No disc preparation, removal of bone or cartilage, or scraping are required before and during formation of the insertion path or insertion of the implant structures 20, so a minimally invasive insertion path sized approximately at or about the maximum outer diameter of the implant structures 20 need be formed. Still, the implant structures 20, which include the elongated bony in-growth or through-growth regions 24, significantly increase the size of the fusion area, from the relatively small surface area of a given joint between adjacent bones, to the surface area provided by an elongated bony in-growth or through-growth regions 24. The implant structures 20 can thereby increase the surface area involved in the fusion and/or stabilization by 3-fold to 4-fold, depending upon the joint involved.

The implant structures 20 can obviate the need for autologous grafts, bone graft material, additional pedicle screws and/or rods, hollow modular anchorage screws, cannulated compression screws, cages, or fixation screws. Still, in the physician's discretion, bone graft material and other fixation instrumentation can be used in combination with the implant structures 20.

The implant structures 20 make possible surgical techniques that are less invasive than traditional open surgery with no extensive soft tissue stripping and no disc removal. The assemblies make possible straightforward surgical approaches that complement the minimally invasive surgical techniques. The profile and design of the implant structures 20 minimize rotation and micro-motion. Rigid implant structures 20 made from titanium provide immediate post-op fusion stability. A bony in-growth region 24 comprising a porous plasma spray coating with irregular surface supports stable bone fixation/fusion. The implant structures 20 and surgical approaches make possible the placement of larger fusion surface areas designed to maximize post-surgical weight bearing capacity and provide a biomechanically rigorous implant designed specifically to stabilize the heavily loaded lumbar spine.

The foregoing is considered as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

I claim:

1. A method for translaminar lumbar fusion comprising creating an insertion path that extends from a superior articular process of a selected lumbar vertebra, cranially through the adjoining facet capsule into a corresponding inferior articular process of an adjacent lumbar vertebra, and, from there, further through the lamina of the adjacent vertebra into an interior opposite posterolateral region adjacent the spinous process of the adjacent vertebra, providing a bone fixation implant comprises an elongated implant structure having a rectilinear cross section including an exterior surface region treated to provide bony in-growth or through-growth along the implant structure, and inserting the bone fixation implant through the insertion path from the superior articular process of the selected lumbar vertebra, cranially through the adjoining facet capsule into the inferior articular process of the adjacent lumbar vertebra, and, from there, further through the lamina of the adjacent vertebra into an interior opposite posterolateral region adjacent the spinous process of the adjacent vertebra.

2. A method according to claim 1 wherein the elongated implant structure has a triangular cross section.

3. A method according to claim 1 wherein the bony in-growth region or through-growth region comprises a porous plasma spray coating on the implant structure.

4. A method according to claim 1 wherein the insertion path is created in a non-invasive manner.

5. A method according to claim 1 wherein the insertion path comprises a bore sized approximately at or approximately about an outer maximum dimension of the bone fixation implant.

6. A method according to claim 1 wherein at least a first implant structure extends from a superior articular process of the selected lumbar vertebra, in a cranial direction through the adjoining facet capsule into the corresponding inferior articular process of the adjacent lumbar vertebra, and, from there, further through the lamina of the adjacent lumbar vertebra into an interior opposite posterolateral region adjacent the spinous process of the adjacent lumbar vertebra, and wherein at least a second implant structure extends from an opposite superior articular process of the selected lumbar vertebra, through the adjoining facet capsule into the corresponding inferior articular process of the adjacent vertebra, and, from there, further through the lamina of the adjacent lumbar vertebra into an interior opposite posterolateral region adjacent the spinous process of the adjacent lumbar vertebra, the first and second implant structures crossing each other within the medial lamina of adjacent lumbar vertebra.

7. A method according to claim 1 wherein the insertion path extends from the superior articular process of lumbar vertebra L5, cranially through the adjoining facet capsule into an inferior articular process of the lumbar vertebra L4, and, from there, further through the lamina of the lumbar vertebra L4 into an interior opposite posterolateral region adjacent the spinous process of the lumbar vertebra L4.

8. A method according to claim 1 wherein at least a first implant structure extends from a left superior articular process of the lumbar vertebra L5, in a cranial direction through the adjoining facet capsule into the corresponding left inferior articular process of the adjacent lumbar vertebra L4, and, from there, further through the lamina of the adjacent lumbar vertebra L4 into an interior right posterolateral region adjacent the spinous process of the adjacent lumbar vertebra L4, and wherein at least a second implant structure extends from a right superior articular process of the selected lumbar vertebra L5, through the adjoining facet capsule into the corresponding right inferior articular process of the adjacent lumbar vertebra L4, and, from there, further through the lamina of the adjacent lumbar vertebra L4 into an interior left posterolateral region adjacent the spinous process of the adjacent lumbar vertebra L4, the first and second implant structures crossing each other within the medial lamina of adjacent lumbar vertebra L4.

9. A system comprising at least one bone fixation implant comprising an elongated implant structure having a rectilinear cross section including an exterior surface region treated to provide bony in-growth or through-growth along the implant structure inserted through an insertion path from a superior articular process of a selected lumbar vertebra, cranially through the adjoining facet capsule into the corresponding inferior articular process of the adjacent lumbar vertebra, and, from there, further through the lamina of the adjacent vertebra into an interior opposite posterolateral region adjacent the spinous process of the adjacent vertebra to affect translaminal lumbar fusion.

10. A system according to claim 9 wherein the elongated implant structure has a triangular cross section.

11. A system according to claim 10 wherein the bony in-growth region or through-growth region comprises a porous plasma spray coating on the implant structure.

12. A system comprising at least a first implant structure comprising an elongated implant structure having a rectilinear cross section including an exterior surface region treated to provide bony in-growth or through-growth along the implant structure inserted through an insertion path from a superior articular process of the selected lumbar vertebra, in a cranial direction through the adjoining facet capsule into the corresponding inferior articular process of the adjacent lumbar vertebra, and, from there, further through the lamina of the adjacent lumbar vertebra into an interior opposite posterolateral region adjacent the spinous process of the adjacent lumbar vertebra, and at least a second implant structure comprising an elongated implant structure having a rectilinear cross section including an exterior surface region treated to provide bony in-growth or through-growth along the implant structure inserted through an insertion path from an opposite superior articular process of the selected lumbar vertebra, through the adjoining facet capsule into the corresponding inferior articular process of the adjacent vertebra, and, from there, further through the lamina of the adjacent lumbar vertebra into an interior opposite posterolateral region adjacent the spinous process of the adjacent lumbar vertebra, the first and second implant structures crossing each other within the medial lamina of adjacent lumbar vertebra to affect translaminal lumbar fusion.

13. A system according to claim 12 wherein the elongated implant structure has a triangular cross section.

14. A system according to claim 12 wherein the bony in-growth region or through-growth region comprises a porous plasma spray coating on the implant structure.

15. A method for lumbar facet fusion comprising creating an insertion path that extends from an inferior articular process of a selected lumbar vertebra, in a caudal direction through the adjoining facet capsule into a corresponding superior articular process of an adjacent lumbar vertebra and into a pedicle of the adjacent lumbar vertebra, providing a bone fixation implant comprising an elongated implant structure having a longitudinal axis and a rectilinear cross section transverse to the longitudinal axis and including an exterior surface region treated to provide bony in-growth or through-growth along the implant structure, and inserting the bone fixation implant through the insertion path from the inferior articular process of the selected lumbar vertebra, in a caudal direction through the adjoining facet capsule into the corresponding superior articular process of the adjacent lumbar vertebra and into a pedicle of the adjacent lumbar vertebra.

16. A method according to claim 15 wherein the elongated implant structure has a triangular cross section.

17. A method according to claim 15 wherein the bony in-growth region or through-growth region comprises a porous plasma spray coating on the implant structure.

18. A method according to claim 15 wherein the insertion path is created in a non-invasive manner.

19. A method according to claim 15 wherein the insertion path comprises a bore sized approximately at or approximately about an outer maximum dimension of the bone fixation implant.

20. A method according to claim 15 wherein at least a first implant structure extends from a left inferior articular process of the selected lumbar vertebra, in a caudal direction through the adjoining facet capsule into the corresponding superior articular process of the adjacent lumbar vertebra and into a pedicle of the adjacent lumbar vertebra, and wherein at least a second implant structure extends from a right inferior articular process of the selected lumbar vertebra, in a caudal direction through the adjoining facet capsule into the corresponding superior articular process of the adjacent lumbar vertebra and into a pedicle of the adjacent lumbar vertebra.

21. A method according to claim 15 wherein at least a first implant structure extends from an inferior articular process of the lumbar vertebra L4, in a caudal direction through the adjoining facet capsule into the corresponding superior articular process of the adjacent lumbar vertebra L5 and into a pedicle of the adjacent lumbar vertebra L5.

22. A method according to claim 15 wherein at least a first implant structure extends from a left inferior articular process of the lumbar vertebra L4, in a caudal direction through the adjoining facet capsule into the corresponding superior articular process of the adjacent lumbar vertebra L5 and into a pedicle of the adjacent lumbar vertebra L5, and wherein at least a second implant structure extends from a right inferior articular process of the selected lumbar vertebra L4, in a caudal direction through the adjoining facet capsule into the corresponding superior articular process of the adjacent lumbar vertebra L5 and into a pedicle of the adjacent lumbar vertebra L5.

23. A system comprising a bone fixation implant comprising an elongated implant structure having a longitudinal axis and a rectilinear cross section transverse to the longitudinal axis and including an exterior surface region treated to provide bony in-growth or through-growth along the implant structure inserted through an insertion path from an inferior articular process of a selected lumbar vertebra, in a caudal direction through the adjoining facet capsule into a corresponding superior articular process of an adjacent lumbar vertebra and into a pedicle of the adjacent lumbar vertebra to affect lumbar facet fusion.

24. A system according to claim 23 wherein the elongated implant structure has a triangular cross section.

25. A system according to claim 23 wherein the bony in-growth region or through-growth region comprises a porous plasma spray coating on the implant structure.

26. A system comprising at least a first implant structure comprising an elongated implant structure having a longitudinal axis and a rectilinear cross section transverse to the longitudinal axis and including an exterior surface region treated to provide bony in-growth or through-growth along the implant structure that extends from a left inferior articular process of a selected lumbar vertebra, in a caudal direction through the adjoining facet capsule into a corresponding superior articular process of an adjacent lumbar vertebra and into a pedicle of the adjacent lumbar vertebra, and at least a second implant structure comprising an elongated implant structure having a rectilinear cross section including an exterior surface region treated to provide bony in-growth or through-growth along the implant structure that extends from a right inferior articular process of the selected lumbar vertebra, in a caudal direction through the adjoining facet capsule into the corresponding superior articular process of the adjacent lumbar vertebra and into a pedicle of the adjacent lumbar vertebra, the first and second implant structures affecting lumbar facet fusion.

27. A system according to claim 26 wherein the elongated implant structure has a triangular cross section.

28. A system according to claim 26 wherein the bony in-growth region or through-growth region comprises a porous plasma spray coating on the implant structure.

* * * * *

UNITED STATES PATENT AND TRADEMARK OFFICE
CERTIFICATE OF CORRECTION

PATENT NO. : 8,444,693 B2
APPLICATION NO. : 12/960811
DATED : May 21, 2013
INVENTOR(S) : Mark A. Reiley It is certified that error appears in the above-identified patent and that said Letters Patent is hereby corrected as shown below:

Title Page, Column 1, Item (63), Related U.S. Application Data, 2nd line; after "now Pat. No. 7,922,765," delete "and a" and insert --which is a--.

Figure 2:
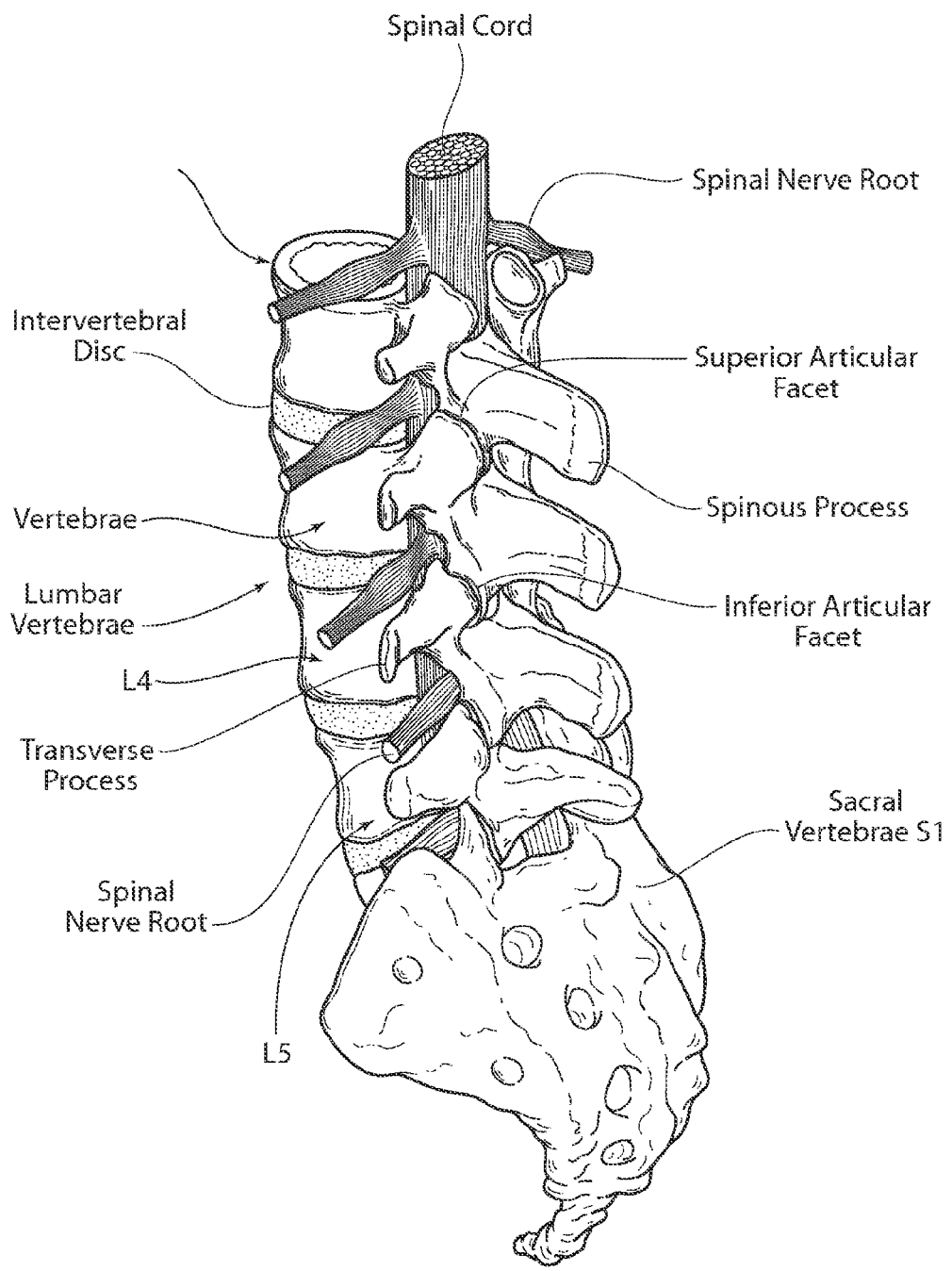
FIG. 2 is an anatomic posterior perspective view of the lumbar region of a human spine, showing lumbar vertebrae L2 to L5 and the sacral vertebrae.
Figure 3:
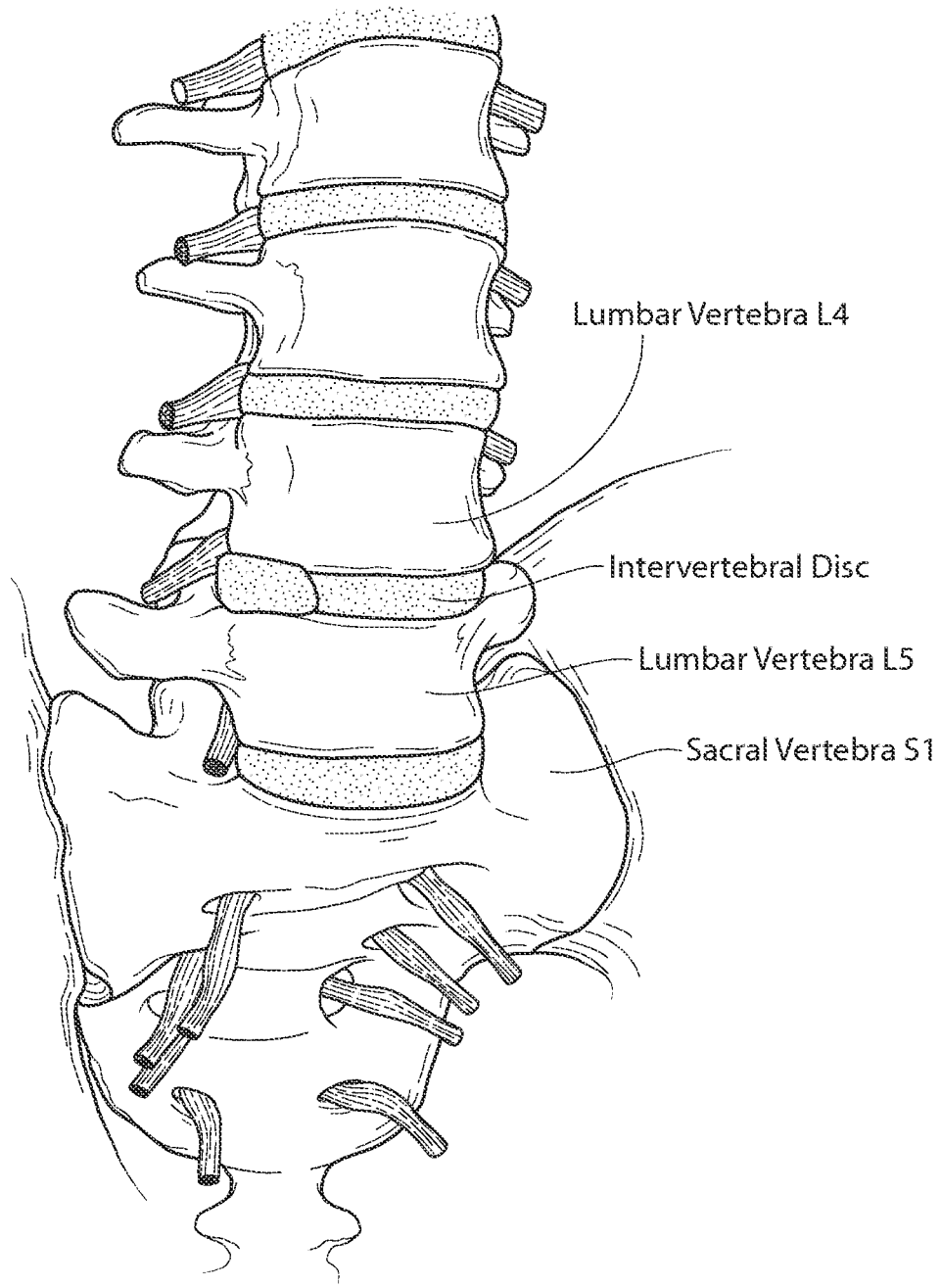
FIG. 3 is an anatomic anterior perspective view of the lumbar region of a human spine, showing lumbar vertebrae L2 to L5 and the sacral vertebrae.

In the Drawings:

Delete drawing sheet 2 and substitute therefor the drawing sheet, consisting of fig. 2 as shown on the attached page.

In the Specifications:

Column 1, line 46; after "The" and before "discs", delete "intervetebral" and insert --intervertebral--.

Column 2, line 1; after L5-S1 and before "When", delete "pondylolisthesis")." and insert --spondylolisthesis).--.

Column 4, line 63; after "anatomic" and before "view", delete "laterial" and insert --lateral--.

Column 6, line 42; after "mesh," and before "or other", delete "hydroxyapetite," and insert --hydroxyapatite,--.

Signed and Sealed this
First Day of October, 2013

Teresa Stanek Rea
*Deputy Director of the United States Patent and Trademark Office*